US009522017B2

(12) United States Patent
Poll et al.

(10) Patent No.: US 9,522,017 B2
(45) Date of Patent: Dec. 20, 2016

(54) DEVICES, SYSTEMS, AND METHODS FOR PERFORMING ENDOSCOPIC SURGICAL PROCEDURES

(75) Inventors: Wayne L. Poll, New Albany, OH (US); Gregory Drach, Liberty Township, OH (US)

(73) Assignee: Minimally Invasive Devices, Inc., Columbus, OH (US)

(*) Notice: Subject to any disclaimer, the term of this patent is extended or adjusted under 35 U.S.C. 154(b) by 201 days.

(21) Appl. No.: 13/311,085

(22) Filed: Dec. 5, 2011

(65) Prior Publication Data

US 2012/0310147 A1    Dec. 6, 2012

Related U.S. Application Data

(60) Provisional application No. 61/419,357, filed on Dec. 3, 2010.

(51) Int. Cl.
*A61M 13/00*    (2006.01)
*A61B 17/34*    (2006.01)

(52) U.S. Cl.
CPC .......... *A61B 17/3417* (2013.01); *A61B 50/30* (2016.02); *A61B 90/361* (2016.02); *A61M 13/00* (2013.01); *A61M 13/003* (2013.01); *A61B 90/70* (2016.02)

(58) Field of Classification Search
CPC ............ A61M 13/00003; A61M 13/00; A61M 13/003; A61B 90/70; A61B 2090/701
See application file for complete search history.

(56) References Cited

U.S. PATENT DOCUMENTS

| 3,373,736 | A | 3/1968 | Fiore et al. |
| D230,727 | S | 3/1974 | Richman |
| 4,207,874 | A | 6/1980 | Choy |
| 4,279,246 | A | 7/1981 | Chikama |
| 4,281,646 | A | 8/1981 | Kinoshita |
| D277,408 | S | 1/1985 | Kubokawa et al. |
| D277,505 | S | 2/1985 | Kubokawa et al. |
| 4,497,550 | A | 2/1985 | Ouchi et al. |
| 4,537,209 | A | 8/1985 | Sasa |
| D280,929 | S | 10/1985 | Lystager |
| 4,548,197 | A | 10/1985 | Kinoshita |

(Continued)

FOREIGN PATENT DOCUMENTS

| EP | 0664101 A1 | 7/1995 |
| EP | 0790652 A1 | 8/1997 |

(Continued)

OTHER PUBLICATIONS

Poll et al.; U.S. Appl. No. 14/308,644 entitled "Sheath for hand-held and robotic laparoscopes," filed Jun. 18, 2014.

(Continued)

*Primary Examiner* — Laura Bouchelle
*Assistant Examiner* — Anh Bui
(74) *Attorney, Agent, or Firm* — Shay Glenn LLP

(57) ABSTRACT

Methods and systems for accessing an operating cavity when performing endoscopic surgery comprising. The systems and methods include at least one obturator-free cannula unit and a trocar assembly. The trocar assembly includes a single dedicated functional obturator independent of the cannula unit and an endoscopic cannula. The invention also provides a system and methods for providing continuous flow of carbon dioxide during a laparoscopic procedure.

10 Claims, 23 Drawing Sheets

(56) References Cited

U.S. PATENT DOCUMENTS

| | | | |
|---|---|---|---|
| 4,552,130 A | 11/1985 | Kinoshita | |
| D284,028 S | 5/1986 | Seager | |
| 4,598,698 A * | 7/1986 | Siegmund | 600/131 |
| 4,616,169 A | 10/1986 | Proffitt | |
| 4,617,013 A | 10/1986 | Betz | |
| 4,633,855 A | 1/1987 | Baba | |
| 4,637,814 A | 1/1987 | Leiboff | |
| 4,646,722 A | 3/1987 | Silverstein et al. | |
| 4,735,603 A | 4/1988 | Goodson et al. | |
| 4,741,326 A | 5/1988 | Sidall et al. | |
| 4,748,970 A | 6/1988 | Nakajima | |
| 4,760,838 A | 8/1988 | Fukuda | |
| 4,773,413 A | 9/1988 | Hussein et al. | |
| 4,794,911 A | 1/1989 | Okada | |
| 4,800,869 A | 1/1989 | Nakajima | |
| 4,877,016 A | 10/1989 | Kantor et al. | |
| 4,941,872 A | 7/1990 | Felix et al. | |
| 4,973,321 A | 11/1990 | Michelson | |
| 4,991,565 A | 2/1991 | Takahashi et al. | |
| 4,998,527 A | 3/1991 | Meyer | |
| 5,009,655 A | 4/1991 | Daignault, Jr. et al. | |
| 5,019,054 A | 5/1991 | Clement et al. | |
| 5,027,791 A | 7/1991 | Takahashi | |
| 5,050,585 A | 9/1991 | Takahashi | |
| 5,133,336 A | 7/1992 | Savitt et al. | |
| 5,144,942 A | 9/1992 | Decarie et al. | |
| 5,147,292 A | 9/1992 | Kullas et al. | |
| 5,163,927 A | 11/1992 | Woker et al. | |
| 5,167,220 A | 12/1992 | Brown | |
| 5,201,908 A | 4/1993 | Jones | |
| 5,207,213 A | 5/1993 | Auhll et al. | |
| 5,225,001 A | 7/1993 | Manni et al. | |
| 5,279,549 A | 1/1994 | Ranford | |
| D346,023 S | 4/1994 | Stewart, Sr. | |
| 5,306,272 A | 4/1994 | Cohen et al. | |
| 5,312,400 A | 5/1994 | Bales et al. | |
| 5,313,934 A | 5/1994 | Wiita et al. | |
| 5,320,091 A | 6/1994 | Grossi et al. | |
| 5,322,070 A * | 6/1994 | Goodman | A61M 13/003 600/431 |
| 5,328,458 A | 7/1994 | Sekino et al. | |
| 5,336,170 A | 8/1994 | Salerno et al. | |
| 5,339,800 A | 8/1994 | Wiita et al. | |
| 5,359,991 A | 11/1994 | Takahashi et al. | |
| 5,364,407 A | 11/1994 | Poll | |
| 5,386,817 A | 2/1995 | Jones | |
| 5,392,766 A | 2/1995 | Masterson et al. | |
| 5,400,767 A | 3/1995 | Murdoch | |
| 5,448,891 A | 9/1995 | Nakagiri et al. | |
| 5,448,990 A | 9/1995 | De Faria Correa | |
| 5,464,008 A | 11/1995 | Kim | |
| 5,468,240 A | 11/1995 | Gentelia et al. | |
| D369,862 S | 5/1996 | Stewart, Jr. | |
| 5,514,074 A | 5/1996 | Yabe et al. | |
| 5,514,084 A | 5/1996 | Fisher | |
| 5,518,502 A | 5/1996 | Kaplan et al. | |
| 5,562,600 A | 10/1996 | Matsuno | |
| 5,563,737 A | 10/1996 | Kamrat | |
| 5,569,157 A | 10/1996 | Nakazawa et al. | |
| 5,575,753 A | 11/1996 | Yabe et al. | |
| 5,575,756 A | 11/1996 | Karasawa et al. | |
| 5,605,532 A | 2/1997 | Schermerhorn | |
| 5,630,795 A | 5/1997 | Kuramoto et al. | |
| 5,637,075 A | 6/1997 | Kikawada | |
| 5,647,840 A | 7/1997 | D'Amelio et al. | |
| 5,697,888 A * | 12/1997 | Kobayashi | A61B 1/00068 137/606 |
| 5,746,695 A | 5/1998 | Yasui et al. | |
| 5,788,628 A | 8/1998 | Matsuno et al. | |
| 5,857,961 A | 1/1999 | Vanden Hoek et al. | |
| 5,865,730 A | 2/1999 | Fox et al. | |
| 5,868,663 A | 2/1999 | Katsurada et al. | |
| 5,869,107 A | 2/1999 | Shimizu et al. | |
| 5,894,369 A | 4/1999 | Akiba et al. | |
| 5,922,105 A | 7/1999 | Fujii et al. | |
| 5,954,637 A | 9/1999 | Francis | |
| 5,957,888 A | 9/1999 | Hinchliffe | |
| 5,989,183 A | 11/1999 | Reisdorf et al. | |
| 6,017,333 A | 1/2000 | Bailey | |
| 6,040,053 A | 3/2000 | Scholz et al. | |
| 6,071,606 A | 6/2000 | Yamazaki et al. | |
| D428,487 S | 7/2000 | Renner et al. | |
| 6,096,026 A | 8/2000 | Schultz | |
| 6,110,103 A | 8/2000 | Donofrio | |
| 6,110,259 A | 8/2000 | Schultz et al. | |
| 6,126,592 A | 10/2000 | Proch et al. | |
| 6,149,659 A | 11/2000 | Ahmed | |
| 6,156,409 A | 12/2000 | Doushita et al. | |
| 6,176,825 B1 | 1/2001 | Chin et al. | |
| 6,206,825 B1 | 3/2001 | Tsuyuki | |
| 6,234,635 B1 | 5/2001 | Seitzinger et al. | |
| 6,282,442 B1 | 8/2001 | DeStefano et al. | |
| 6,293,909 B1 | 9/2001 | Chu et al. | |
| 6,299,592 B1 | 10/2001 | Zander | |
| 6,306,932 B1 | 10/2001 | Yamamoto et al. | |
| 6,354,992 B1 | 3/2002 | Kato | |
| 6,361,492 B1 | 3/2002 | Santilli | |
| 6,383,134 B1 | 5/2002 | Santilli | |
| 6,409,657 B1 | 6/2002 | Kawano | |
| 6,425,535 B1 | 7/2002 | Akiba | |
| 6,447,446 B1 | 9/2002 | Smith et al. | |
| 6,582,357 B2 | 6/2003 | Ouchi et al. | |
| 6,589,316 B1 | 7/2003 | Schultz et al. | |
| D481,126 S | 10/2003 | Hayamizu | |
| 6,645,197 B2 | 11/2003 | Garrison et al. | |
| D484,594 S | 12/2003 | Hayamizu | |
| D486,910 S | 2/2004 | Hayamizu et al. | |
| 6,695,772 B1 | 2/2004 | Bon et al. | |
| 6,699,185 B2 | 3/2004 | Gminder et al. | |
| 6,712,479 B1 | 3/2004 | Seitzinger et al. | |
| 6,712,757 B2 | 3/2004 | Becker et al. | |
| 6,712,759 B2 | 3/2004 | Muller | |
| 6,752,755 B2 | 6/2004 | Akiba | |
| 6,755,782 B2 | 6/2004 | Ogawa | |
| D493,529 S | 7/2004 | Hayamizu et al. | |
| 6,764,445 B2 | 7/2004 | Ramans et al. | |
| 6,780,516 B2 | 8/2004 | Chen | |
| 6,783,845 B2 | 8/2004 | Zhang et al. | |
| D498,846 S | 11/2004 | Hayamizu et al. | |
| 6,814,697 B2 | 11/2004 | Ouchi | |
| 6,857,436 B2 | 2/2005 | Labib et al. | |
| 6,858,005 B2 | 2/2005 | Ohline et al. | |
| 6,882,236 B2 | 4/2005 | Dinn et al. | |
| 6,889,400 B2 | 5/2005 | Kawazoe et al. | |
| 6,921,362 B2 | 7/2005 | Ouchi | |
| 6,921,380 B1 | 7/2005 | Epstein et al. | |
| 6,977,053 B2 | 12/2005 | Mukasa et al. | |
| 6,984,204 B2 | 1/2006 | Akiba | |
| 6,989,183 B2 | 1/2006 | McKillip | |
| 7,074,180 B2 | 7/2006 | Bertolero et al. | |
| 7,080,641 B2 | 7/2006 | Gomez | |
| 7,087,013 B2 | 8/2006 | Belson et al. | |
| 7,150,713 B2 | 12/2006 | Shener et al. | |
| D534,655 S | 1/2007 | Iranyi et al. | |
| D535,743 S | 1/2007 | Williams | |
| 7,169,167 B2 | 1/2007 | Chu | |
| 7,198,599 B2 | 4/2007 | Goto et al. | |
| 7,223,231 B2 | 5/2007 | Akiba | |
| 7,250,028 B2 | 7/2007 | Julian et al. | |
| 7,270,670 B1 | 9/2007 | Yencho | |
| 7,341,556 B2 | 3/2008 | Shalman | |
| D573,711 S | 7/2008 | Johnson et al. | |
| 7,413,543 B2 | 8/2008 | Banik et al. | |
| D600,807 S | 9/2009 | Dienst et al. | |
| D613,403 S | 4/2010 | Poll et al. | |
| 7,803,109 B2 | 9/2010 | Gomez | |
| 7,803,144 B2 | 9/2010 | Vollrath | |
| 7,927,271 B2 | 4/2011 | Dimitriou et al. | |
| 8,047,215 B1 | 11/2011 | Sasaki | |
| 8,062,214 B2 | 11/2011 | Shener et al. | |
| 8,075,481 B2 | 12/2011 | Park et al. | |
| 8,096,944 B2 | 1/2012 | Harrel | |
| 8,226,549 B2 | 7/2012 | Kumar et al. | |
| 8,419,624 B2 | 4/2013 | James et al. | |

(56) References Cited

U.S. PATENT DOCUMENTS

| | | | |
|---|---|---|---|
| 8,517,921 B2 | 8/2013 | Tremaglio et al. | |
| 8,545,395 B2 | 10/2013 | Akahoshi et al. | |
| 2001/0011162 A1 | 8/2001 | Epstein | |
| 2002/0022762 A1 | 2/2002 | Beane et al. | |
| 2002/0058858 A1 | 5/2002 | Ogura et al. | |
| 2002/0072652 A1 | 6/2002 | Berci et al. | |
| 2002/0091304 A1 | 7/2002 | Ogura et al. | |
| 2002/0193806 A1 | 12/2002 | Moenning et al. | |
| 2003/0200738 A1 | 10/2003 | Booth | |
| 2004/0034339 A1 | 2/2004 | Stoller et al. | |
| 2004/0059363 A1 | 3/2004 | Alvarez et al. | |
| 2004/0082915 A1 | 4/2004 | Kadan | |
| 2004/0204671 A1 | 10/2004 | Stubbs et al. | |
| 2005/0043683 A1 | 2/2005 | Ravo | |
| 2005/0059981 A1 | 3/2005 | Poll | |
| 2005/0065405 A1 | 3/2005 | Hasegawa | |
| 2005/0080342 A1 | 4/2005 | Gilreath et al. | |
| 2005/0113797 A1 | 5/2005 | Ott et al. | |
| 2005/0119528 A1 | 6/2005 | Weinberg | |
| 2005/0137529 A1 | 6/2005 | Mantell | |
| 2005/0154355 A1 | 7/2005 | Gross et al. | |
| 2005/0159765 A1 | 7/2005 | Moutafis et al. | |
| 2005/0171467 A1 | 8/2005 | Landman | |
| 2005/0171528 A1 | 8/2005 | Sartor et al. | |
| 2005/0203342 A1 | 9/2005 | Kucklick et al. | |
| 2005/0234301 A1 | 10/2005 | Gomez | |
| 2005/0261553 A1 | 11/2005 | Swain et al. | |
| 2006/0020165 A1 | 1/2006 | Adams | |
| 2006/0041186 A1 | 2/2006 | Vancaillie | |
| 2006/0047184 A1 | 3/2006 | Banik et al. | |
| 2006/0052661 A1 | 3/2006 | Gannot et al. | |
| 2006/0069306 A1 | 3/2006 | Banik et al. | |
| 2006/0252993 A1 | 11/2006 | Freed et al. | |
| 2006/0270910 A1 | 11/2006 | Davis | |
| 2007/0088275 A1* | 4/2007 | Stearns | A61B 17/3421 604/164.01 |
| 2007/0179432 A1* | 8/2007 | Bar Or | A61B 1/00068 604/30 |
| 2007/0182842 A1 | 8/2007 | Sonnenschein et al. | |
| 2007/0203474 A1 | 8/2007 | Ryan et al. | |
| 2007/0282253 A1 | 12/2007 | Sasaki | |
| 2007/0289449 A1 | 12/2007 | Roberts et al. | |
| 2007/0299310 A1 | 12/2007 | Phillips | |
| 2008/0021277 A1 | 1/2008 | Stefanchik et al. | |
| 2008/0051631 A1 | 2/2008 | Dejima et al. | |
| 2008/0081948 A1 | 4/2008 | Weisenburgh et al. | |
| 2008/0086704 A1 | 4/2008 | Aravamudan | |
| 2008/0108871 A1 | 5/2008 | Mohr | |
| 2008/0161646 A1 | 7/2008 | Gomez | |
| 2008/0188715 A1 | 8/2008 | Fujimoto | |
| 2008/0200765 A1 | 8/2008 | Mondschein | |
| 2008/0208128 A1 | 8/2008 | Guo et al. | |
| 2008/0249362 A1 | 10/2008 | Jiang et al. | |
| 2008/0255419 A1 | 10/2008 | Kendale et al. | |
| 2008/0319266 A1 | 12/2008 | Poll et al. | |
| 2009/0018602 A1 | 1/2009 | Mitelberg et al. | |
| 2009/0113644 A1 | 5/2009 | Heck | |
| 2009/0215018 A1 | 8/2009 | Edmondson et al. | |
| 2009/0234193 A1 | 9/2009 | Weisenburgh et al. | |
| 2009/0253962 A1 | 10/2009 | Fernandez et al. | |
| 2009/0253965 A1 | 10/2009 | Miyamoto | |
| 2010/0168520 A1 | 7/2010 | Poll et al. | |
| 2010/0198014 A1 | 8/2010 | Poll et al. | |
| 2010/0331856 A1 | 12/2010 | Carlson et al. | |
| 2012/0022331 A1 | 1/2012 | Poll et al. | |
| 2012/0101337 A1 | 4/2012 | Clark et al. | |
| 2012/0165610 A1 | 6/2012 | Poll et al. | |
| 2012/0184897 A1 | 7/2012 | Poll | |
| 2012/0197084 A1 | 8/2012 | Drach et al. | |
| 2013/0317295 A1 | 11/2013 | Morse | |
| 2014/0114128 A1 | 4/2014 | Wills | |
| 2015/0374212 A1 | 12/2015 | Drach et al. | |
| 2016/0089006 A1 | 3/2016 | Poll et al. | |
| 2016/0174828 A1 | 6/2016 | Drach et al. | |

FOREIGN PATENT DOCUMENTS

| | | |
|---|---|---|
| EP | 1188415 A2 | 3/2002 |
| JP | 59-203534 | 11/1984 |
| JP | 61-168328 | 7/1986 |
| JP | 05-103756 A | 4/1993 |
| JP | 05-199979 | 8/1993 |
| JP | H07-275185 A | 10/1995 |
| JP | 09-135804 | 5/1997 |
| JP | 2000-225093 | 8/2000 |
| JP | 2004-267583 A | 9/2004 |
| JP | 2005-110978 | 4/2005 |
| JP | 2009-240596 A | 10/2009 |
| WO | WO92/10969 A1 | 7/1992 |
| WO | WO92/22238 A1 | 12/1992 |
| WO | WO2005/002210 A1 | 1/2005 |
| WO | WO2005/009227 A1 | 2/2005 |
| WO | WO2005/115221 A1 | 12/2005 |
| WO | WO2006/014814 A1 | 2/2006 |
| WO | WO2008/030256 A1 | 3/2008 |
| WO | WO2008/077080 A2 | 6/2008 |
| WO | WO2008/128142 A2 | 10/2008 |
| WO | WO2008/130582 A2 | 10/2008 |
| WO | WO2009/073577 A2 | 6/2009 |
| WO | WO2010/042913 A2 | 4/2010 |
| WO | WO2010/042915 A2 | 4/2010 |
| WO | WO2011/041387 A1 | 4/2011 |
| WO | WO2011/044448 A2 | 4/2011 |
| WO | WO2011/130399 A1 | 10/2011 |
| WO | WO2012/005819 A1 | 1/2012 |
| WO | WO2012/044410 A2 | 4/2012 |
| WO | WO2012/122263 A2 | 9/2012 |

OTHER PUBLICATIONS

Ott, Douglas E.; Chapter 1. Pneumoperitoneum: Production, management, effects and consequences; in Prevention & Management of Laparoendoscopic Surgical Complications, 1st Ed.; 6 pgs.; Jan. 1999 (retrieved from: http://laparoscopy.blogs.com/prevention_management/2006/02/chapter_1_pneum.html on Oct. 7, 2013).

Poll et al.; Design U.S. Appl. No. 29/329,224 entitled "Manifold Coupling," filed Dec. 10, 2008 (now abandoned).

Poll et al.; Design U.S. Appl. No. 29/329,225 entitled "Sheath Manifold for Maintaining Surgical Scope Visualization," filed Dec. 10, 2008 (now abandoned).

Poll et al.; Design U.S. Appl. No. 29/329,221 entitled "Handle for Maintaining Surgical Scope Visualization," filed Dec. 10, 2008 (now abandoned).

Poll et al.; Design U.S. Appl. No. 29/335,699 entitled "Surgical Scope Stabilizer," filed Apr. 20, 2009 (now abandoned).

Farley et al.; Double-blind, prospective, randomized study of warmed, humidified carbon dioxide insufflation vs standard carbon dioxide for patients undergoing lararoscopic cholecystectomy; Arch Surg; 139; pp. 739-744; Jul. 2004.

Hashimoto et al.; Development of a fogless scope and its analysis using infrared radiation pyrometer; Surg Endosc; 11(8); pp. 805-808; Aug. 1997.

Lawrentschuk et al.; Laparoscopic lens fogging: A review of etiology and methods to maintain a clear visual field; Journal of Endourology; 24(6); pp. 905-913; Jun. 2010.

Ohdaira et al.; Antifogging effects of a socket-type device with the superhydrophilic, titanium dioxide coated glass for laparoscope; Surg endosc; 21(2); pp. 333-338; Dec. 2007.

Poll et al.; U.S. Appl. No. 14/490,501 entitled "Systems and methods for optimizing and maintaining visualization of a surgical field during the use of surgical scopes," filed Sep. 18, 2014.

International Search Report and Written Opinion for PCT/US11/63277, dated Jul. 10, 2012.

Poll et al.; U.S. Appl. No. 14/733,752 entitled "View optimizer and stabilizer for use with surgical scopes," filed Jun. 8, 2015.

Poll et al.; U.S. Appl. No. 14/733,672 entitled "Device for maintaining visualization with surgical scopes," filed Jun. 8, 2015.

\* cited by examiner

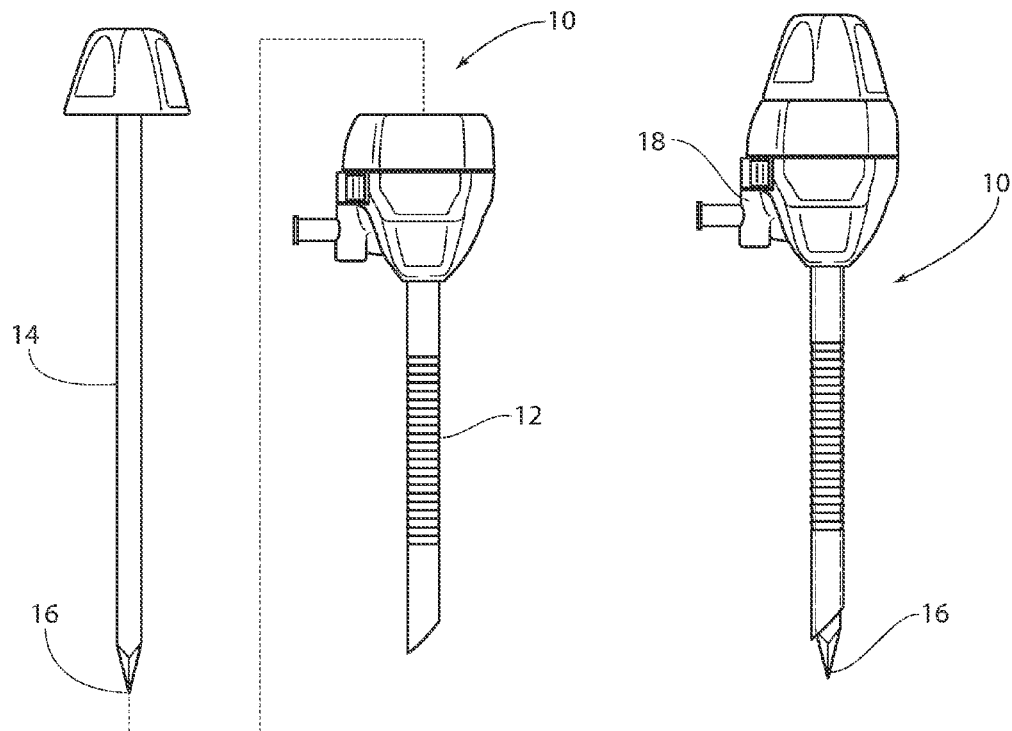
*Fig. 1A*
PRIOR ART
*Fig. 1B*
PRIOR ART
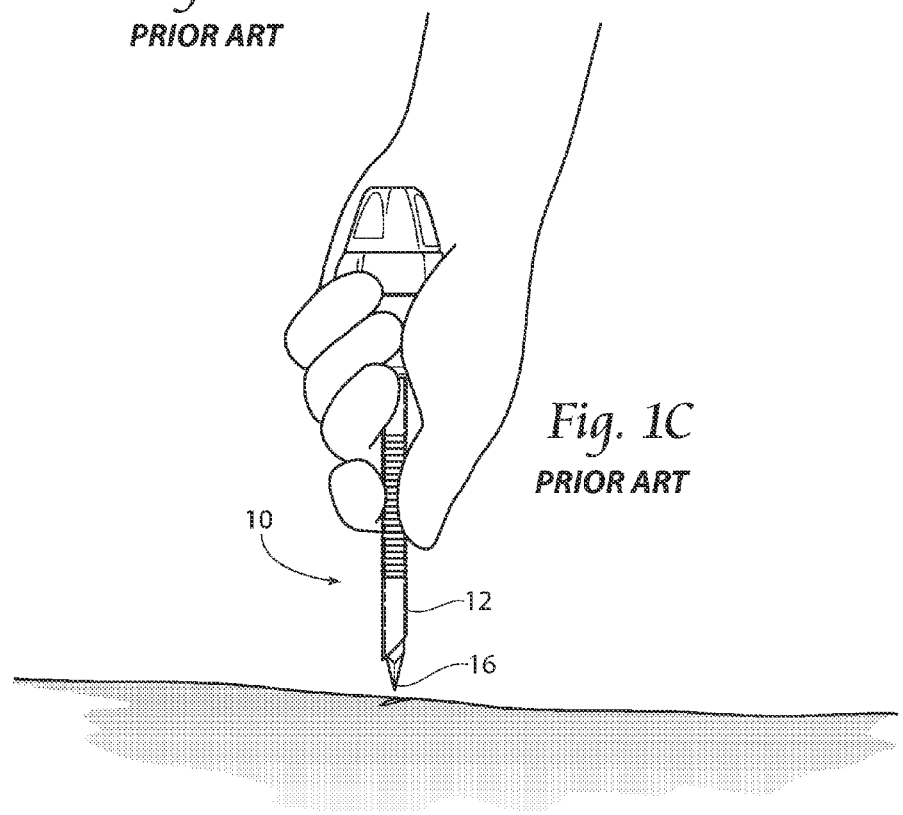
*Fig. 1C*
PRIOR ART

Insufflator Pressure

DEVICES, SYSTEMS, AND METHODS FOR PERFORMING ENDOSCOPIC SURGICAL PROCEDURES

RELATED APPLICATION

This application claims the benefit of provisional patent application Ser. No. 61/419,357 filed 3 Dec. 2010.

FIELD OF THE INVENTION

The invention generally relates to devices, systems, and methods for performing endoscopic surgical procedures.

BACKGROUND OF THE INVENTION

Endoscopic surgery (also called keyhole surgery) encompasses modern, minimally invasive surgical procedures, in which access to the surgical field is gained through relatively small incisions. Endoscopic surgery includes laparoscopic procedures, which are performed within the abdominal or pelvic cavities. Endoscopic surgery also includes thoracoscopic procedures, which are performed on the thoracic or chest cavity.

Minimally invasive surgical procedures are desirable because they make possible reduced blood loss; reduced post-operative patient discomfort; shortened recovery and hospitalization time; and reduced exposure of internal organs to possible contaminants.

In laparoscopic surgery, for example, operations in the abdomen are performed through relatively small incisions (usually 0.5-1.5 cm).

During laparoscopic surgery, the abdomen is inflated using $CO_2$ gas provided by an insufflation circuit. The $CO_2$ elevates the abdominal wall above the internal organs like a dome to create a working and viewing space for the surgery.

One key element in laparoscopic surgery is an assembly called a laparoscopic trocar (which, in short hand, will be called an "LT"). A conventional LT 10 is shown in FIGS. 1A and 1B. The LT 10 is an access device used to penetrate the wall of the abdominal cavity to provide access for the introduction of $CO_2$ insufflation gas; the manipulation of surgical instruments; and the insertion of optics (called laparoscopes) to observe the operating field while surgery is performed. A conventional LT 10 is typically treated as a single use, disposable item.

A conventional LT 10 consists of two parts (see FIG. 1A): a cannula 12 and an obturator 14.

The cannula 12 is a tubular sleeve that defines an access path or lumen to the operating field. The cannula typically includes a self-contained "air-lock" mechanism within the lumen, which provides access for surgical instruments and optics through the cannula, while preventing the escape of $CO_2$ introduced into the abdominal cavity, so the cavity stays inflated.

According to existing laparoscopic surgical preference and practice, conventional laparoscopic surgical instruments and laparoscopes are typically sized and configured in one of three standard exterior diameters, the smallest being about 5 mm, the next larger being about 10 mm, and the largest being about 12 mm. Due to inventory and cost issues, the conventional LT's incorporate cannulas 12 accordingly sized in a range of standard interior diameters to accommodate the smooth and airtight passage of the conventional 5 mm, or 10 mm, or 12 mm instruments. This hierarchy of cannula sizes for conventional LT's imposes limitation upon the use of specialized instruments having desirable added functional benefits, but which increase the exterior diameter of the instrument.

The obturator 14 is an elongated pointed cylinder with a sharpened, tissue-penetrating tip. The obturator 14 is sized and configured to fit within the lumen of a conventionally-sized cannula 12, with the penetrating tip 16 protruding from the open end of the cannula lumen, as FIG. 1B shows. The protruding, penetrating tip 16 of the obturator 14 incises or separates tissue on entry so as to allow body penetration.

In conventional usage, the LT 10 is supplied as an assembled unit, as shown in FIG. 1B, including the cannula 12 and a dedicated obturator 14 inserted through the lumen of the cannula. To penetrate the abdominal wall, the surgeon manipulates the cannula 12 and dedicated obturator 14 as a single assembled unit (see FIG. 1C). Once penetration has been made, the dedicated obturator 14 is withdrawn (see FIG. 1D), opening the lumen of the cannula 12 for passage of instruments or optics.

Since conventional LT's are typically treated as single use items, after each obturator 14 is withdrawn from its companion cannula 12 as just described, the obturator 14 is not used again during the procedure. It is discarded as medical waste. Theoretically, an obturator 14 (and companion cannula 12) could, if desired, be reprocessed for use in a subsequent procedure, but, according to conventional wisdom, many surgeons and surgical teams nevertheless resist reusing devices intended for single use that, even though reprocessed, have been inside a previous patient.

Typically, during a single laparoscopic procedure, several, separate LT's (each comprising a cannula 12 and its own dedicated obturator 14) are inserted (see FIG. 1E). For example, at least one LT 10 is inserted for the introduction of $CO_2$ insufflation gas (the cannula 12 includes a stopcock 18 communicating with a passage in the cannula 12, to which an insufflation line can be coupled); one or more LT's are inserted for passage of surgical instruments; and at least one LT is inserted for the passage of a laparoscope. The separate LT's (each comprising a cannula 12 and its dedicated obturator 14) are inserted individually, one at a time, in sequence, to provide the desired number of abdominal penetrations; and, in sequence, the withdrawn obturators 14 are put aside, one at a time, for disposal. Thus, at the end of the procedure (see FIG. 1E), the number of obturators 14 that are discarded as medical waste equals the number of cannulas 12 that form the abdominal penetrations.

TECHNICAL FEATURES OF THE INVENTION

One aspect of the invention provides a simplified system and method for performing an endoscopic surgical procedure. The system and method are particularly well suited for use, e.g., in a situation in which it is desirable to make use of a specialized endoscopic instrument, which provides one or more desirable functional benefits, but which possesses a marginally increased exterior diameter that does not readily fit the cannula sizes used by conventional LT's.

The system and method include a single or a plurality of individual endoscopic cannula units to provide an array of access sites for minimally invasive endoscopic access to and/or visualization of a targeted internal operating field. There is no functional obturator preassembled to any cannula unit to aid insertion of the cannula unit into tissue. Each cannula unit is supplied obturator-free. Each cannula unit is sized and configured to accommodate passage of a conventional trocar assembly.

For installing every cannula unit, the system and method include a single trocar assembly sized to pass through the cannula unit. The trocar assembly includes a preassembled single endoscopic cannula and a single dedicated functional obturator. The system and method make possible the repeated use of the single trocar assembly to aid insertion of multiple cannula units into tissue, establishing an array of multiple endoscopic access sites using a single trocar assembly as the only obturator. The system and method make possible significantly less environmental damage due to medical waste, as well as contribute to lowered health care costs.

Another aspect of the invention provides another simplified system and method for performing an endoscopic surgical procedure. The system and method are directed head-on to the solution of the problem of excess medical waste and unnecessary medical equipment costs associated with conventional endoscopic procedures. The system and method provide single use cannula units sized and configured to accommodate a conventional endoscopic instrument (e.g., 5 mm, or 10 mm, or 12 mm); however, none of the cannula units is mated or made available with its own obturator. The cannula units are each provided obturator-free and are installed in multiple arrays using but a single conventional functional obturator. The single functional obturator is itself supplied as part of a preassembled conventional LT of the same size, which can be provided as a kit along with one or more cannula units or separately from another source. The system and method make it possible to establish an array of multiple endoscopic access sites (comprising the cannula units and the cannula of the LT) using only a single functional obturator.

The systems and methods described provide, for the first time, a plurality of stand-alone, single use endoscopic cannula units, free of their own dedicated obturators, that can be installed either by use of a preassembled single trocar preassembly or by use of a single functional obturator during a given surgical procedure. The result is, for a given endoscopic procedure entailing the installation of several cannula access units, the need for only one functional obturator. Cost savings and less environmental damage result.

BRIEF DESCRIPTION OF THE DRAWINGS

FIGS. 1A to 1E are views of a conventional laparoscopic trocar and its method of use.

DESCRIPTION OF THE PREFERRED EMBODIMENTS

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Multiple Endoscopic Access Systems and Methods Employing a Single Obturator

A. First Representative Embodiment (An Overview)

Figure 2:
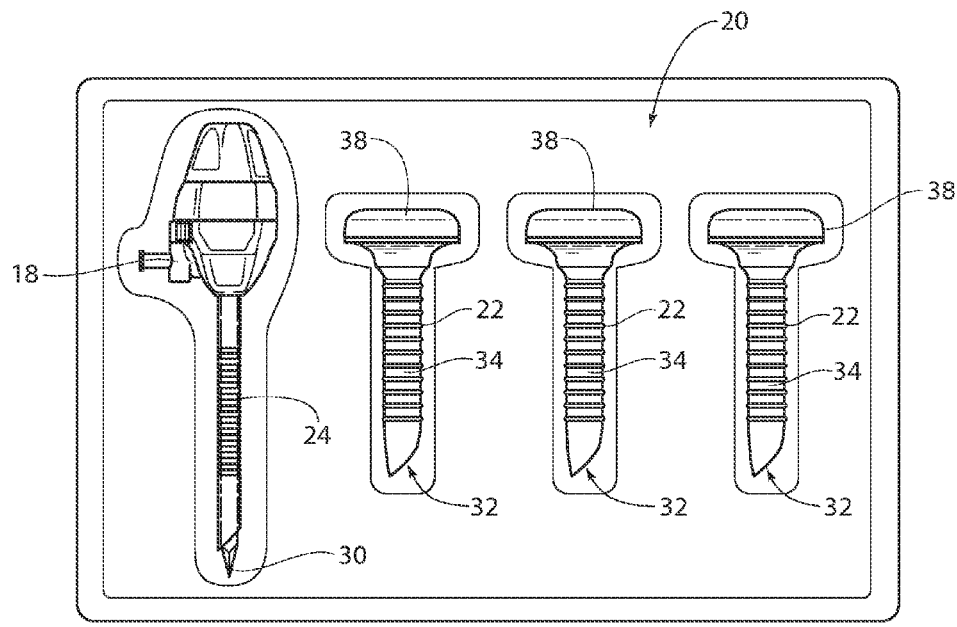
FIG. 2 is a view of a simplified system for performing an endoscopic surgical procedure that makes possible the installation of multiple non-conventional cannula units using a single conventional functional obturator.

FIG. 2 shows a simplified system 20 for performing an endoscopic surgical procedure. The system 20 is particularly well suited for use in a situation in which it is desirable to make use of a specialized endoscopic instrument, which provides one or more desirable functional benefits, but which possesses a marginally increased exterior diameter that falls between the cannula sizes used by conventional LT's. For example, and as will be described by example in greater detail later, a given specialized endoscopic instrument having desirable features may require a 7-8 mm access site, which is too large to fit a conventional 5 mm LT, and small enough to not require a conventional 10 mm LT. In the hierarchy of cannula sizes for conventional LT's, cannulas suitable for a 7-8 mm instrument are available but are not uniformly stocked by hospitals, and when they are, they require their own dedicated obturators. The system 20 solves this problem by providing a non-conventional cannula unit 22 to accommodate a marginally larger endoscopic instrument (e.g., 7 to 8 mm), which can be installed using a single smaller diameter conventional LT (e.g., 5 mm), which is then used at another puncture site once the marginally larger cannula unit 22 has been set and the smaller LT withdrawn. The system's solution also makes possible the installation of multiple non-conventional cannula units 22 using a single conventional functional obturator. The result is significantly less medical waste, as well as lowered health care equipment costs.

More particularly, the system 20 includes a plurality of individual endoscopic cannula units 22 as will be described in greater detail later. The cannula units 22 provide an array of access sites for minimally invasive endoscopic access to and/or visualization of a targeted internal operating field. As shown in FIG. 2, there is no functional obturator preassembled to any cannula unit 22 to aid insertion of the cannula unit into tissue. Each cannula unit 22 is supplied obturator-free.

The system 20 also include a single trocar assembly 24. The trocar assembly 24 includes a single endoscopic cannula 26, which provides one additional site for endoscopic access to the operating field. The trocar assembly 24 also includes, for the cannula 26, a single dedicated functional obturator 28 to aid insertion of the trocar assembly 24 as a unit into tissue. The single dedicated functional obturator 28 of the trocar assembly is the only functional obturator the system 20 provides.

As will be described in greater detail later, each endoscopic cannula unit 22 of the system is sized and configured to be marginally larger in internal diameter than the largest external diameter of the single trocar assembly 24. This makes possible the repeated use of the single trocar assembly 24 to aid insertion of all cannula units 22 into tissue. The system 20 makes possible a method for establishing an array of multiple endoscopic access sites using a single trocar assembly 24 as the only obturator, resulting in significantly less environmental damage due to medical waste, as well as contributing to lowered health care costs.

1. The Single Trocar Assembly

Figure 3A:
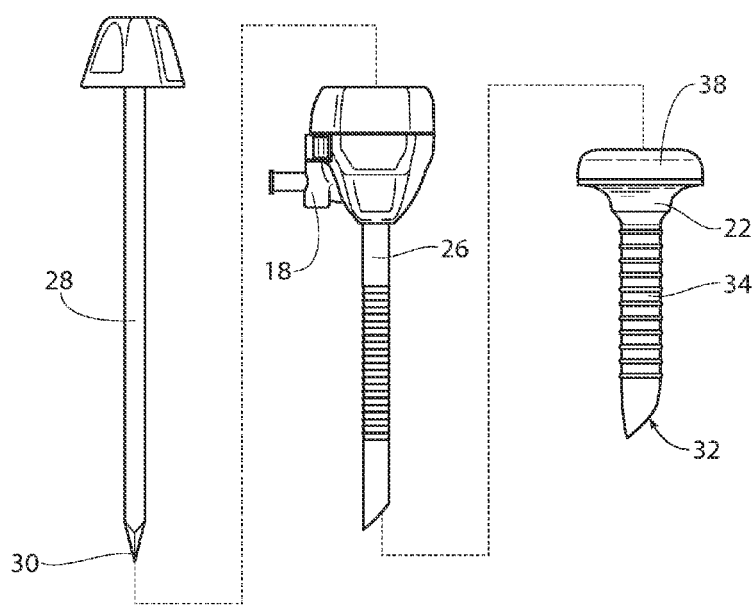
FIG. 3A is an exploded view of components of the system shown in FIG. 2, comprising a cannula unit, an endoscopic cannula, and a dedicated functional obturator for the endoscopic cannula.
Figure 3B:
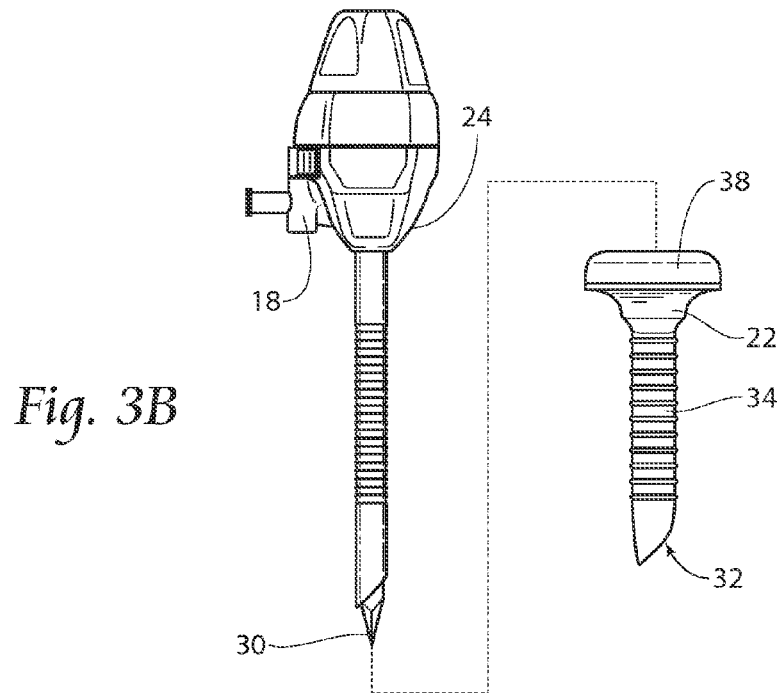
FIG. 3B is a partially assembled view of components of the system shown in FIG. 2, comprising the cannula unit, and a trocar assembly comprising the dedicated functional obturator inserted into the endoscopic cannula.

The single endoscopic trocar assembly 24 comprises a single endoscopic cannula 26 and a single, dedicated functional obturator 28, as shown in FIG. 3A, which are provided preassembled with the system 20, as FIGS. 2 and 3B show. Alternatively, a trocar assembly 24 can be provided separately and later used in association with one or more cannula units 22 (also separately supplied).

The endoscopic cannula 26 can be conventionally sized to accommodate, upon removal of the dedicated obturator 28, conventional endoscopic tools and the attachment of an insufflations line. Both components of the single endoscopic trocar assembly 24 are intended to be used once during a given procedure, and thereafter discarded or, if desired, reprocessed.

By "functional obturator," it is meant that obturator 28 includes a pointed or conical, tissue piercing tip 30, which is sized and configured, during passage in tissue, to incise or separate tissue. By "trocar assembly" with a "dedicated functional obturator," it is meant that the single functional obturator 28 is supplied pre-assembled with the single endoscopic cannula 26, such that the pointed or conical, tissue piercing tip 30 of the obturator 28 is oriented to aid the insertion of the endoscopic trocar assembly 24 as a unit into tissue.

In the illustrated embodiment, the single functional obturator 28 is pre-assembled in a sliding fit within a lumen of the single endoscopic cannula 26 (see FIG. 3B), to form the trocar assembly 24. When fitted within the lumen, the pointed or conical, tissue piercing tip 30 of the obturator 28 protrudes from an open distal end of the lumen to incise or separate tissue in advance of the distal end of the endoscopic cannula 26. As shown in FIGS. 3A and 3B, the distal end of the endoscopic cannula 26 can itself be funnel shaped to aid the insertion of the trocar preassembly as a unit into tissue.

The trocar assembly 24 can be a conventional, off-the-shelf LT, having a cannula diameter that is common in the practice of endoscopic procedures, e.g., 5 mm; 10 mm; or 12 mm.

2. The Cannula Units

The endoscopic cannula units 22 are each individually sized and configured to provide a site of minimally invasive, endoscopic access to a targeted internal operating field, e.g., within an abdomen.

By "cannula unit," it is meant that a given cannula unit 22 is not supplied with its own dedicated functional obturator. That is, the system provides the ability to create multiple endoscopic access sites (i.e., using the multiple cannula units 22 and the single trocar assembly 24), but provides for use of only a single functional obturator. The single functional obturator for the multiple cannula units 22 is the endoscopic trocar assembly 24 itself.

As FIG. 3B shows, each endoscopic cannula unit 22 comprises a tubular sleeve that defines an interior lumen 32. A given cannula unit 22 can be formed by molding or machining from a biocompatible plastic or metal material. When fabricated from plastic material, the cannula unit can be transparent or opaque. The exterior of a cannula unit can include a ribbed outer profile 34 to take purchase in tissue, and can further include loops (not shown) for the passage of sutures to secure the cannula unit 22 to tissue during use. The cannula units 22 are intended to be disposable, low cost items, to be used once during a given procedure, and thereafter discarded.

Figure 3C:
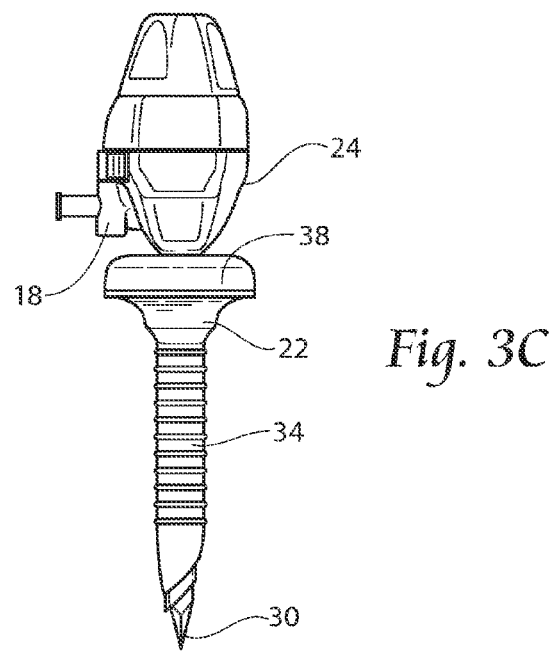
FIG. 3C is a fully assembled view of components of the system shown in FIG. 2, comprising the trocar assembly inserted into the cannula unit, forming a concentric access assembly.

As FIG. 3C shows, the interior diameter of the lumen 32 of the cannula unit 22 is purposefully sized and configured to be slightly larger than the exterior diameter of the endoscopic cannula 26 of trocar assembly 24, to smoothly and tightly accommodate passage of the entire trocar assembly 24 through the lumen 32 of the cannula unit 22. For example, if the trocar assembly 24 has a 5 mm outside diameter, the interior diameter of the cannula unit 22 can be marginally larger, e.g., 7.5 to 8 mm. The interior lumen 32 of each cannula unit 22 has a maximum axial length that is equal to or less than the maximum axial length of the endoscopic cannula 26 of the trocar assembly 24.

Thus, each endoscopic cannula unit 22 can be individually fitted for insertion, one at a time, concentrically over the entire pre-assembled endoscopic trocar assembly 24, with the dedicated functional obturator 28 of the trocar assembly 24 protruding beyond both the endoscopic cannula 26 of the trocar assembly 24 and the separate cannula unit 22. That is, a given cannula unit 22 can be fitted over the exterior cannula 26 of the trocar assembly 24, to which the dedicated functional obturator 28 is pre-assembled. The result is that the single trocar assembly 24 can itself be repeatedly reused during the span of a given procedure as the only functional obturator to install multiple cannula units 22.

In a representative embodiment (see FIGS. 3B and 3C), the cannula unit 22 includes a distal working region having an interior lumen 32 (the working lumen) sized and configured to provide an access site through which the single trocar assembly 24 can pass. For example, for use in association with a 5 mm (internal diameter, but with a larger external diameter) trocar assembly 24, the interior diameter of the working lumen 32 of the cannula unit can be about 7.5 to 8 mm.

In a representative embodiment (see FIGS. 4A, 4B, and 4C), the cannula unit 22 further includes a proximal region that includes a gas seal assembly 36. The gas seal assembly 36 serves to prevent loss of insufflation gas from the operating cavity through the working lumen 32 of the cannula unit 22, either when no instrument occupies the working lumen 32 or when an instrument occupies the working lumen 32.

The gas seal assembly 36 can be variously sized and configured.

Figures 4A, 4B, 4C:
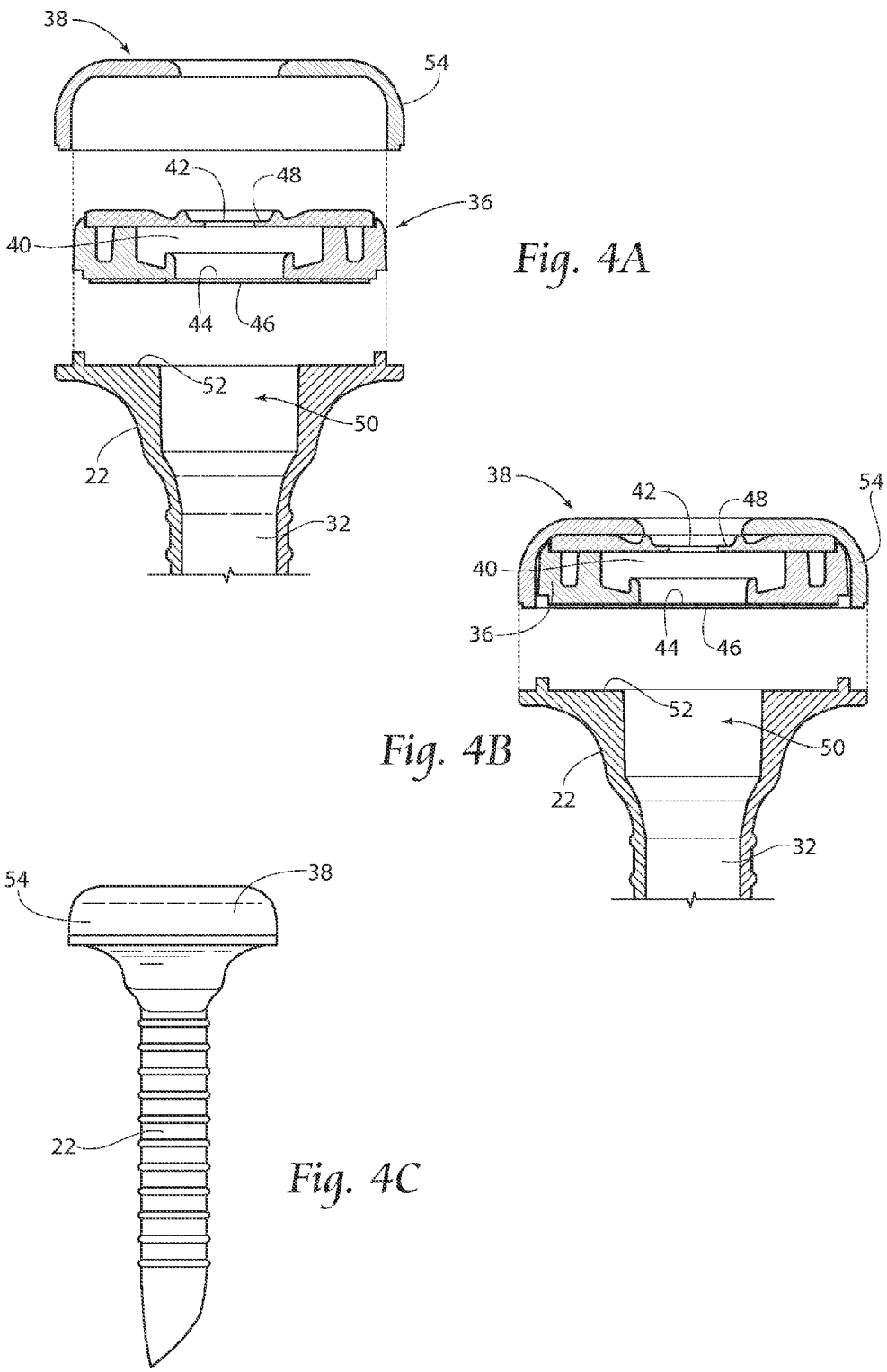
FIGS. 4A and 4B are fully and partially exploded views of the gas seal assembly that forms a part of the cannula unit that is a component of the system shown in FIG. 2.
FIG. 4C is an elevation, fully assembled view of the cannula unit that is a component of the system shown in FIG. 2.

In a representative embodiment (see FIG. 4C), a cap 38 spans the proximal region of the cannula unit 22. As shown in FIG. 4A, the cap 38 includes a working passage 40, which, when fitted to the proximal region, is axially aligned with the working lumen 32 of the cannula unit 22. As best shown in FIG. 4A, the working passage 40 includes an entry orifice 42 on the proximal end of the cap 38 and an exit orifice 44 within the cap 38. As FIG. 5B shows, an instrument I can be inserted into the entry orifice 42 and through the working passage 40 to the exit orifice 44, and thus into and through the working lumen 32 of the cannula unit 22.

In this arrangement, the gas seal assembly 36 is housed entirely within the cap 38 in-line with the working passage 40. In a representative embodiment, the gas seal assembly 36 desirably includes two cooperating functional seals 46 and 48. A first function seal 46 is positioned near the exit orifice 44. A second functional seal 48 is positioned near the entry orifice 42.

Figure 5A:
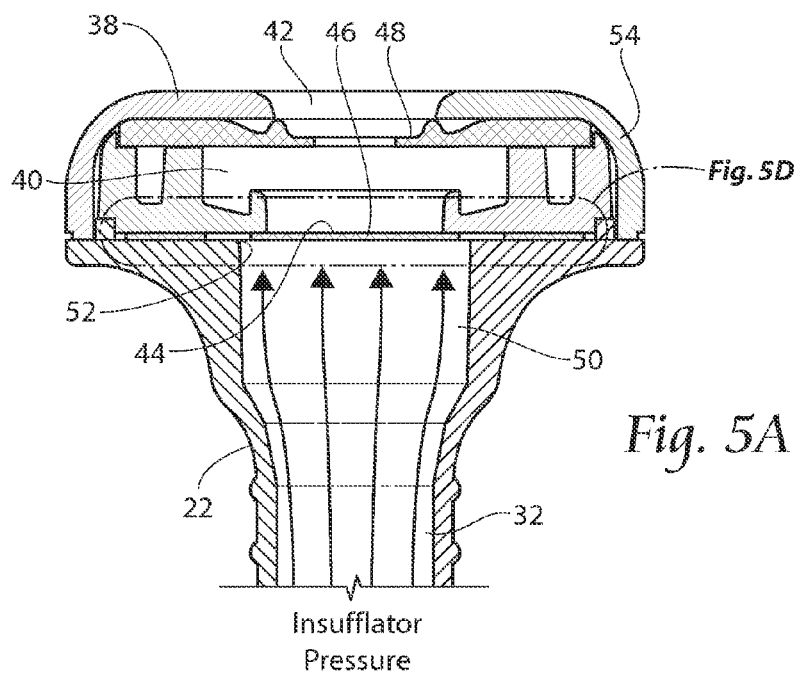
FIG. 5A is an enlarged section view of the gas seal assembly shown in FIGS. 4A and 4B, before insertion of an endoscopic instrument.

The first functional seal 46 is sized and configured to normally prevent gas loss when an instrument I is not inserted through the working passage 40, i.e., when the working lumen 32 of the cannula unit 22 is unoccupied (see FIG. 5A). The first functional seal 46 is also sized and configured to yield during the insertion of an instrument I through the working passage 40 into the working lumen 32, and desirably without obstructing the insertion (see FIG. 5B).

Figure 5B:
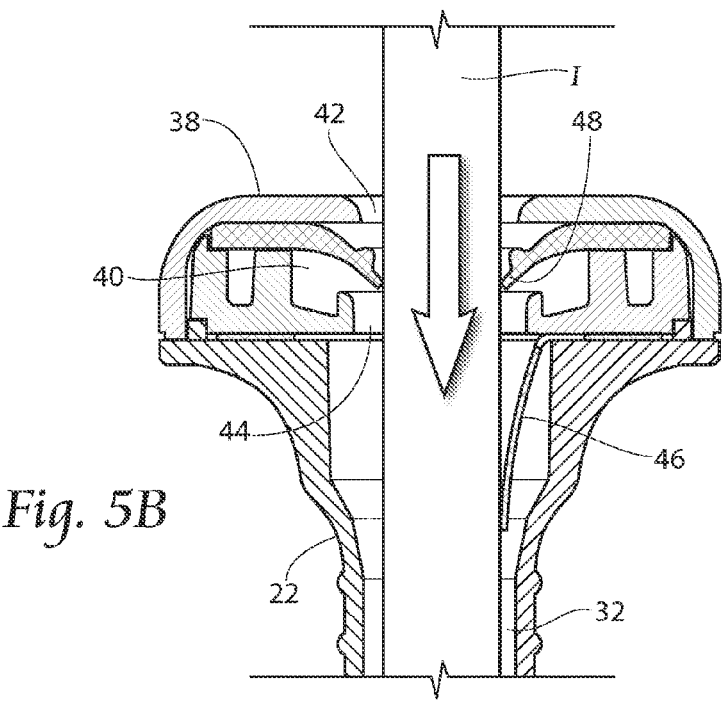
FIG. 5B is an enlarged section view of the gas seal assembly shown in FIGS. 4A and 4B, during insertion of an endoscopic instrument.

The second functional seal 48 is sized and configured to prevent gas loss as the first functional seal 48 yields to the insertion of an instrument I through the working passage 40 into the working lumen 32 of the cannula unit 22 (as shown in FIG. 5B). However, upon removal of the instrument I from the working passage 40 (see FIG. 5C), the first functional seal 46 is sized and configured to quickly return from its yielded condition to its normal condition, again preventing gas loss.

As a result, there is no gas loss through the working lumen 32 of the cannula unit 22 as the cannula unit 22 serves its purpose of providing minimally invasive access to the insufflated operating cavity.

The size and configuration of the cooperating first and second functional seals 46 and 48 can vary.

In a representative embodiment, the first functional seal 46 comprises a flap valve component located adjacent the exit orifice 44 of the working passage 40 (see FIG. 4C). The flap valve component 46 is movable, in the absence of an instrument I occupying the exit orifice (as FIG. 5A shows), to a flap closed condition in response to exposure to typical insufflation pressure (e.g., 15 mmHg) in the working lumen 32. In the flap closed condition, the flap valve component 46 closes and seals the exit orifice 44, as FIG. 5A shows. In this way, the flap valve component 46 prevents gas loss when an instrument I is not inserted through the exit orifice 44.

As FIG. 5B shows, the flap valve component 46 is pushed away from the flap closed condition in response to the insertion of an instrument I through the exit orifice 44 and thus through the flap valve component 46 itself. The flap valve component 46 is sized and configured to flexibly yield to the passage of the instrument I, without damage to the flap valve component 46 and preferably without obstructing the instrument's passage, which is what FIG. 5B shows.

Figure 5C:
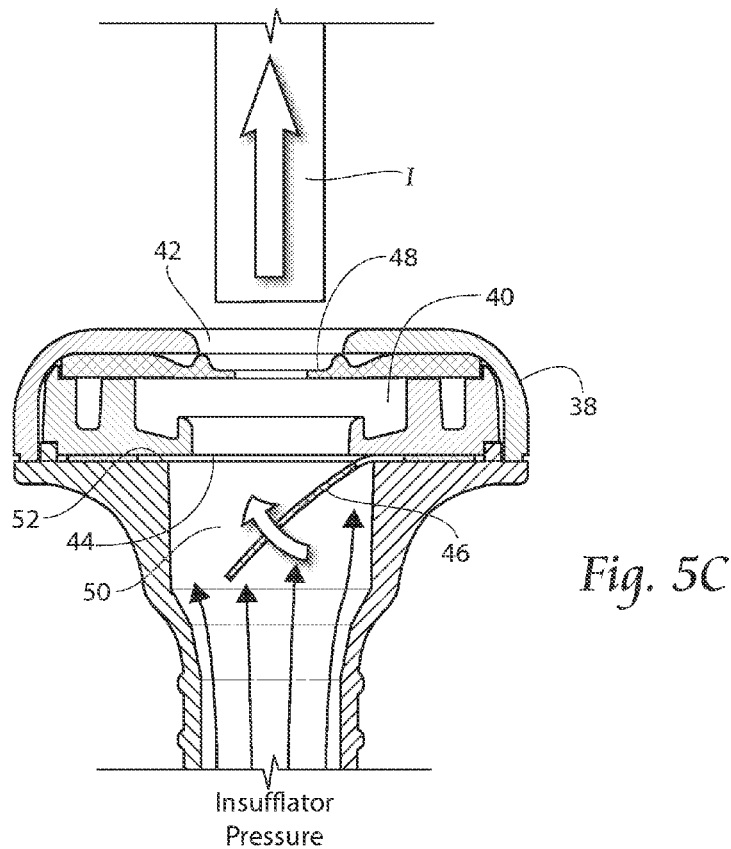
FIG. 5C is an enlarged section view of the gas seal assembly shown in FIGS. 4A and 4B, during withdrawal of an endoscopic instrument.

As shown in FIG. 5C, upon removal of the instrument I from the exit orifice 44 (and thus freeing the flap valve component 46), the flap valve component 46 returns to the flap closed condition in response to exposure to insufflation pressure in the now-unoccupied working lumen 32 of the cannula unit 22.

The diameter of flap valve component 46 is selectively sized and configured relative to the diameter of the exit orifice 44 to effectively cover and seal the exit orifice 44 in response to a typical range of insufflation pressures. In a representative embodiment, for an exit orifice 44 having a diameter of 0.4", a flap valve component 46 having a diameter 0.5" will affect a desired seal.

Further, the proximal region of the lumen of the cannula unit is desirably sized and configured to form a pressure directing chamber 50 immediately distal to the flap valve component 46. The pressure directing channel 50 accommodates and complements the fit and function of the flap valve component 46, as its condition is affected by insufflation pressures and the passage of instruments.

Figure 5D:
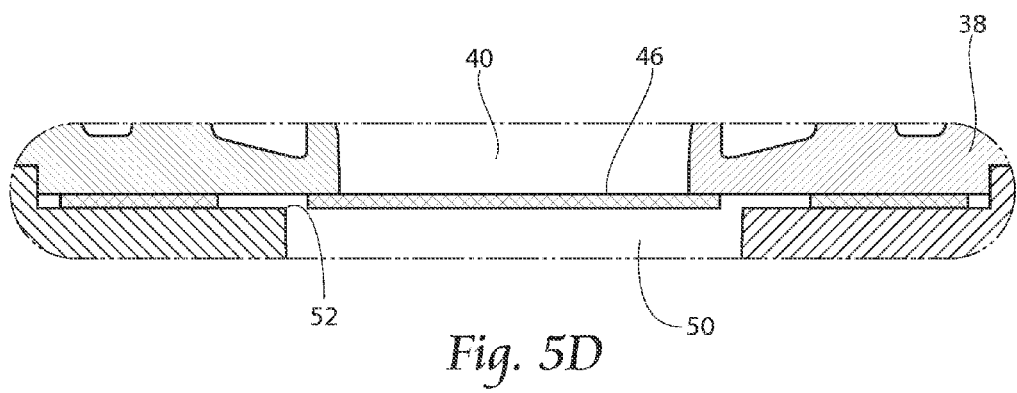
FIG. 5D is an enlarged section view of the first functional seal of the gas seal assembly shown in FIGS. 5A to 5C.

In a representative embodiment (see FIGS. 5A and 5D), pressure directing chamber 50 enlarges the radial dimensions of the working channel 32 in the vicinity of the flap valve component 46, and is further elongated axially to accommodate, without interference and damage, the movement of the flap valve component 46 between its closed and yield conditions. The radial enlarged chamber 50 desirably terminates near the exit orifice 44 to define a sharp lip edge 52 bounding the flap valve component 46 in generally the same plane as the flap valve component 46 (see FIG. 5D). As FIG. 5A shows, the lip edge 52 directs gas in the chamber 50 uniformly upward against the flap valve component 46, and not around the flap valve component 46, thereby minimizing vibration of the flap valve component 46 when closed or closing. The uniform pressure applied upwardly by the chamber 50 maintains a closed and sealed exit orifice 44 in the absence of an instrument I. The upward flow of gas through the chamber 50 also aids the rapid return of the flap valve component 46 to the closed condition upon removal of an instrument I from the exit orifice, as FIG. 5C shows.

The material type, thickness, and durometer of the flap valve component 46 can be further selected to optimize the fit and function of the flap valve component 46 in the presence of a range of typical insufflation pressures. In a representative embodiment, the flap valve component 46 is made, e.g., of a polyurethane material having a durometer of from 85 to 90 shore A. In this embodiment, the flap valve component 46 relies upon a combination of the focused application of insufflation pressure and the material properties of the flap valve component 46 itself to seal the exit orifice 44.

In this arrangement, the second functional seal 48 comprises an elastomeric septum located adjacent the entrance orifice 42 of the working passage 40. The elastomeric septum 48 is sized and configured to create a sliding seal along the instrument I as it passes through the entrance orifice.

In a representative embodiment (see FIGS. 4A and 4B, the gas seal assembly 36 comprises a low profile unitary body 54, made possible by the unique first (gas) functional seal 46 and second (instrument) functional seal 48 combination, which is unlike the duckbill and cone seals used in most commercially available trocars. The unitary body 54 is formed (e.g., by molding or machining plastic or metal materials) with the working passage 40, the entrance orifice 42, and the exit orifice 44 integrally formed. The first and second functional seals 46 and 48 are attached to the unitary body 54. The gas seal assembly 36 can then be inserted as a unit into the cap 38. As a result, the cap 38 itself can be low-profile (e.g., in a representative embodiment, an axial height of 0.4 in).

3. Representative Method of Use

The unique functional features of each cannula unit as described make possible a unique method of establishing an array of multiple endoscopic access sites using only a single functional obturator. FIGS. 6A to 6I show a representative method that makes use of these features.

The method includes (see FIG. 6A) (i) providing a single endoscopic trocar assembly 24 comprising a single endoscopic cannula 26 and a single, dedicated functional obturator 28, as described above.

The method further includes (see FIG. 6B) (ii) providing one or more endoscopic cannula units 22, as described above, free of (i.e., without) its own dedicated functional obturator. Each cannula unit 22 has a minimum interior diameter sized and configured to smoothly and tightly accommodate passage of the endoscopic cannula 26, which forms the exterior of the single trocar assembly 24. The cannula unit 22 has a maximum axial length that is equal to or less than the maximum axial length of the endoscopic cannula 26 of the trocar assembly 24.

The method further includes (see FIG. 6C) (iii) selecting a single one of the cannula units 22 for inserting into tissue to provide a site of minimally invasive, endoscopic access to a targeted internal operating field.

Figure 6A:
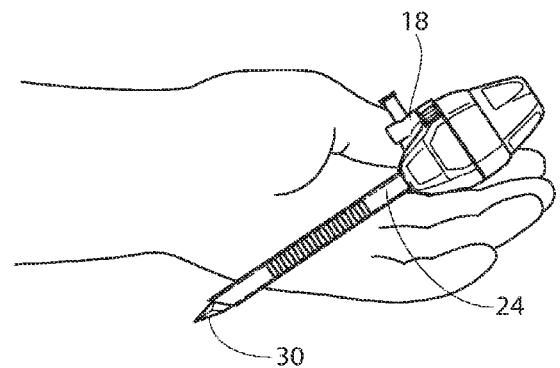
FIGS. 6A to 6I are a sequence of views showing a representative method of using the simplified system shown in FIG. 2.
Figure 6B:
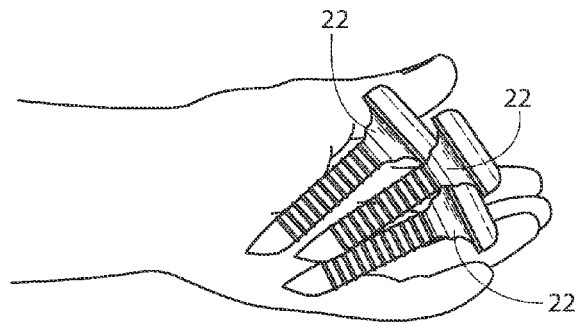
Figure 6C:
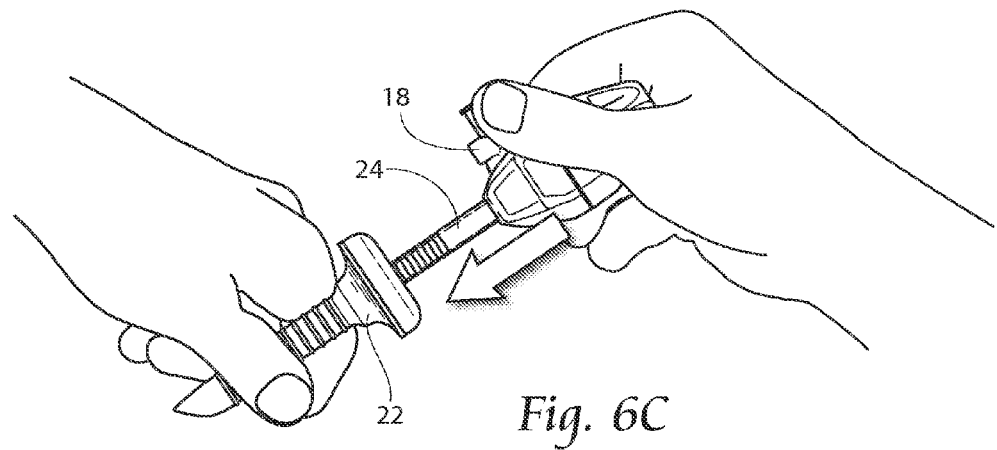
Figure 6D:
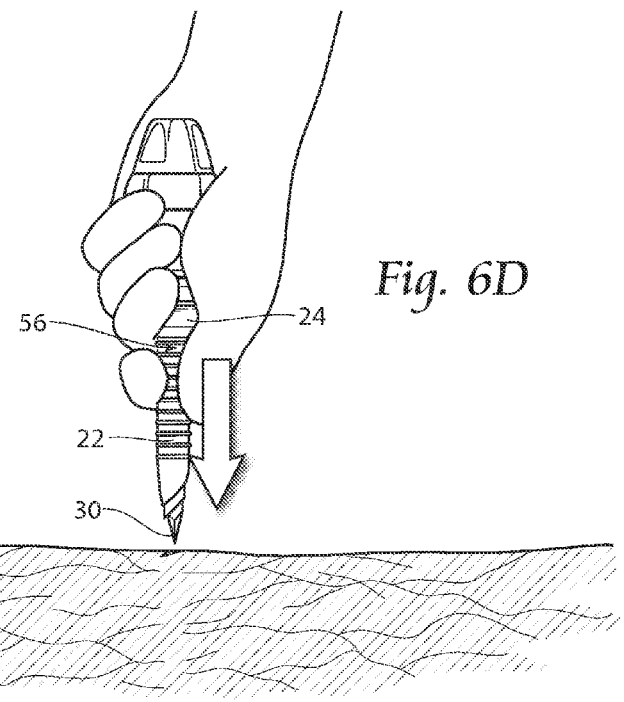
Figure 6E:
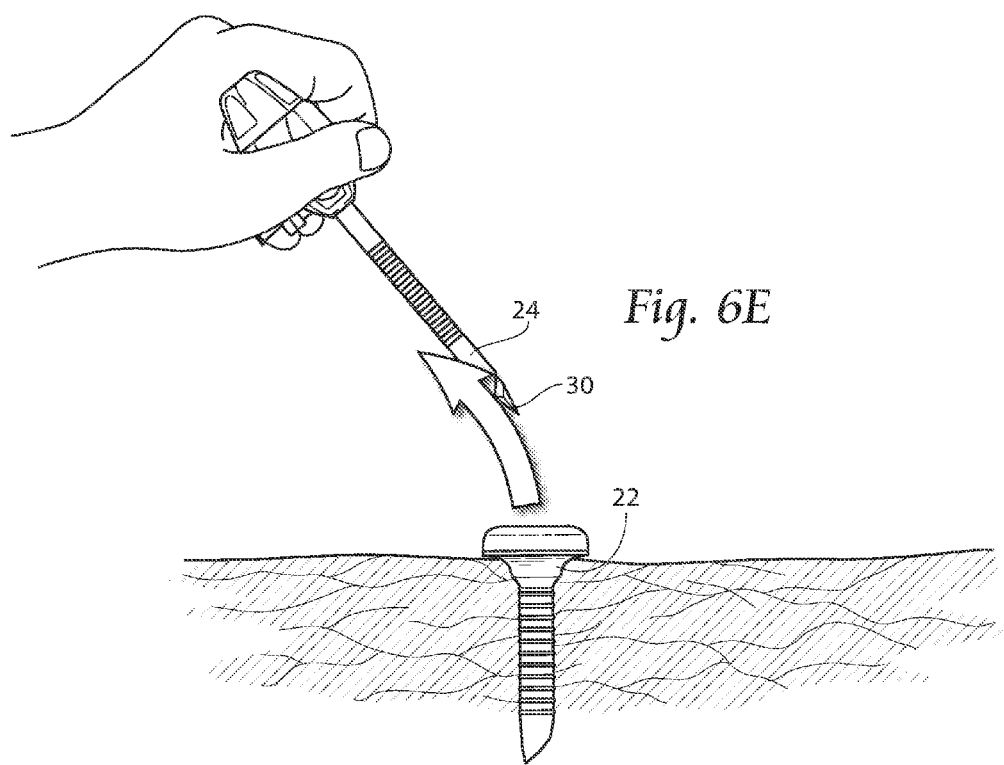
Figure 6F:
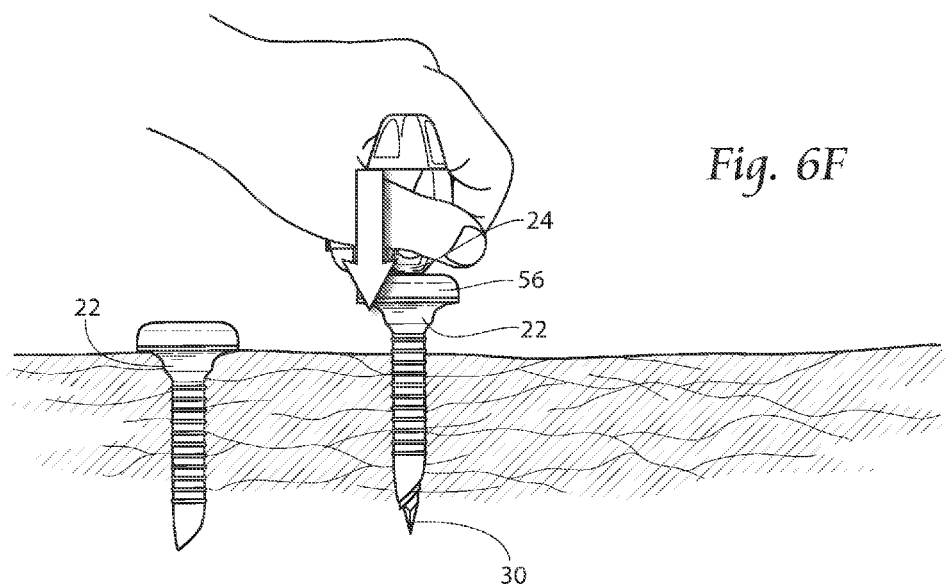
Figure 6G:
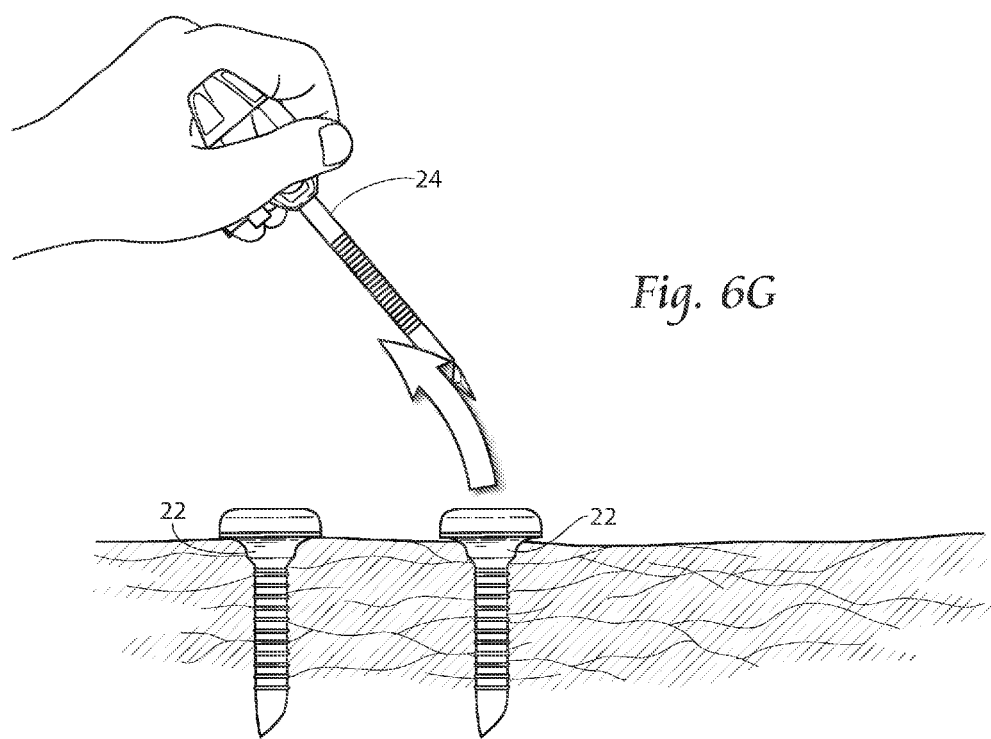

As FIG. 6D further shows, the method further includes (iv) fitting the selected cannula unit 22 over the entire single trocar assembly 24.

By fitting the cannula unit 22 over the entire trocar assembly 24, a concentric access assembly 56 for the cannula unit 22 is created. The concentric access assembly 56 comprises, from interior to exterior, the dedicated functional obturator 28 of the trocar assembly 24, the endoscopic cannula 26 of the trocar assembly 24, and the selected cannula unit 22. The concentric access assembly 56 includes, protruding beyond the distal end of the cannula unit 22, the penetrating tip 30 of a functional obturator 28.

The method further includes (see FIG. 6D) (v) manipulating the concentric access assembly 56 as an integrated unit into tissue, allowing the protruding, penetrating tip 30 of the functional obturator to incise or separate tissue to achieve body penetration. At this stage in the procedure, an insufflation line can be connected to a stopcock 18 conventionally provided on the trocar assembly 24, to pressurize the operating cavity.

The method further includes, after body penetration and insufflation have been made (see FIG. 6E), (vi) withdrawing the trocar assembly 24 from the cannula unit 22, leaving the cannula unit 22 in place providing access to the operating cavity. The gas seal assembly 36 in the cannula unit 22, as above described, prevents loss of insufflation pressure as the method progresses.

The method optionally includes, after (vi) (see FIGS. 6F and 6G) the repeated reuse of the single trocar assembly 24 to install any desired number of selected cannula units 22 to provide any desired number of abdominal penetrations. For each abdominal penetration (see FIG. 6F), a given cannula unit 22 is fitted concentrically over the entire trocar assembly 24 to form a concentric access assembly 56 that includes the additionally selected cannula unit 22. The concentric access assembly 56 is again manipulated as a single unit, allowing the protruding, penetrating tip 30 of the functional obturator 28 to again incise or separate tissue to again achieve body penetration. Once penetration has been made (see FIG. 6G), the trocar assembly 24 is withdrawn from the cannula unit 22. Another selected cannula unit 22 remains to provide additional access to the operating cavity.

Figure 6H:
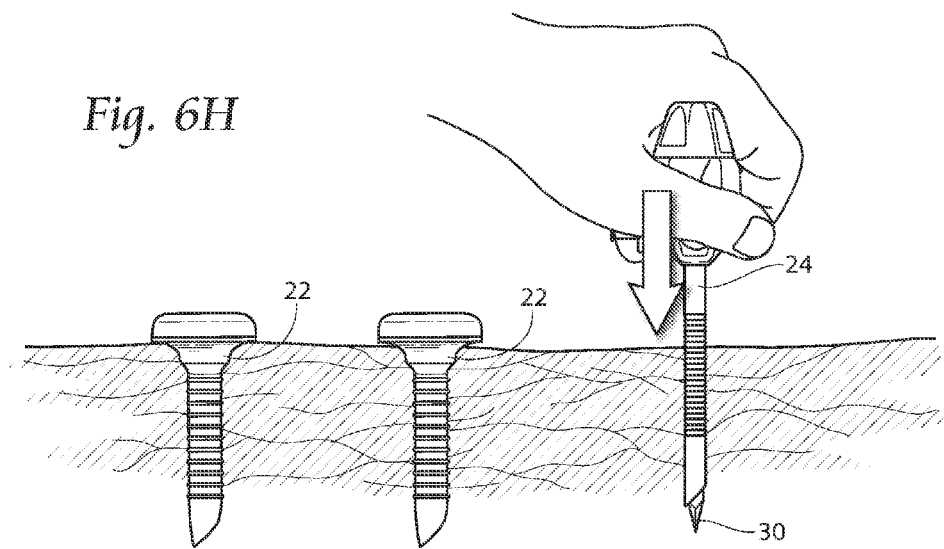

The method further includes, after insertion of all desired cannula units 22, the use of the trocar assembly 24 by itself in a traditional manner for form yet another access site. As shown in FIG. 6H, the method includes (vii) manipulating the trocar assembly 24 as an integrated unit into tissue, this time without a cannula unit 22, allowing the protruding, penetrating tip 30 of the functional dedicated obturator 28 to incise or separate tissue to achieve body penetration for the cannula 26. The method further includes, after body penetration has been made (see FIG. 6I), (viii) withdrawing the dedicated functional obturator 28 of the trocar assembly 24 from the endoscopic cannula 26 of the trocar assembly 24, leaving the endoscopic cannula 26 of the trocar assembly 24 in place providing additional access to the operating cavity and/or for the couples of insufflations pressure (to the stopcock 18).

Figure 1D:
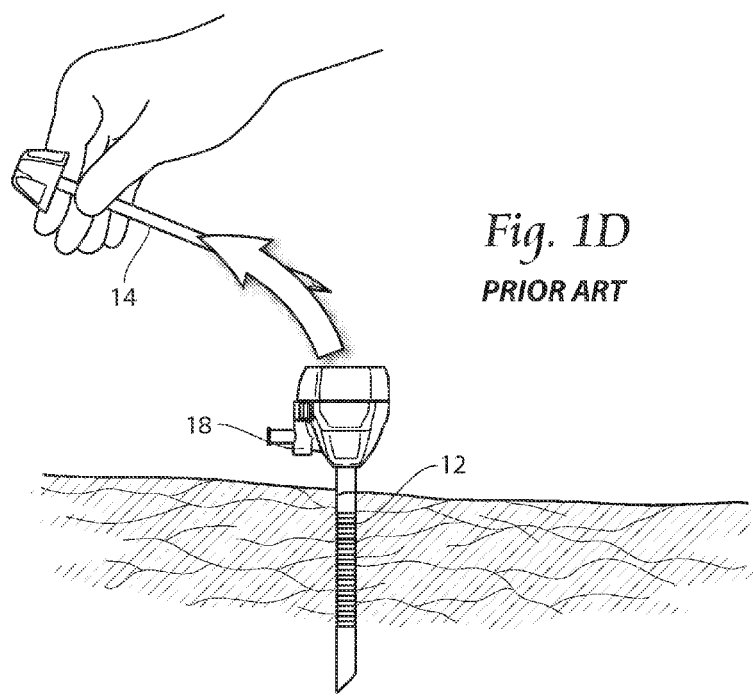
Figure 1E:
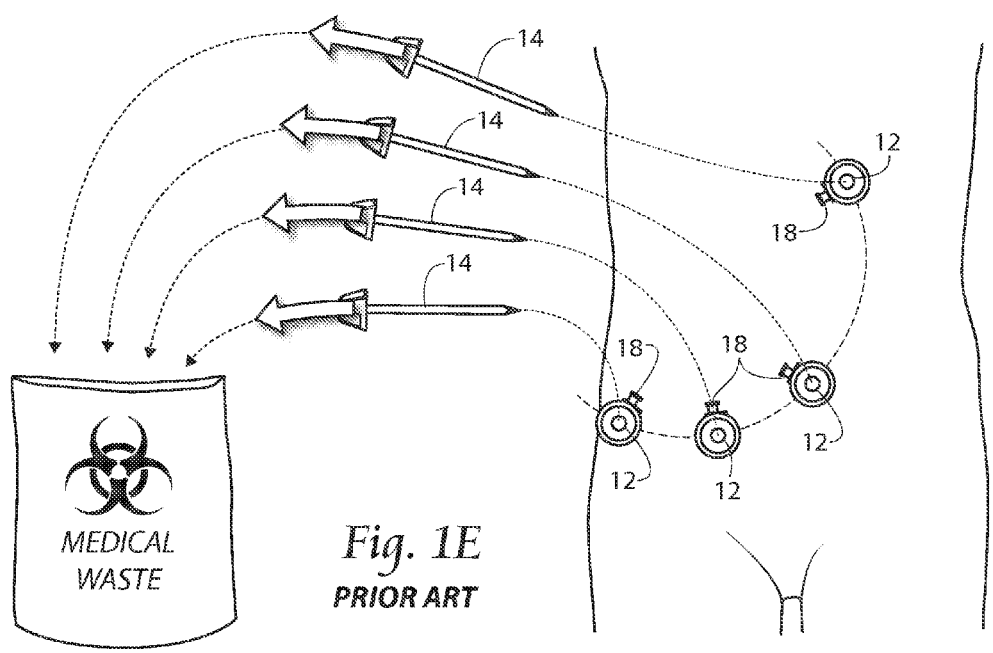
Figure 6I:
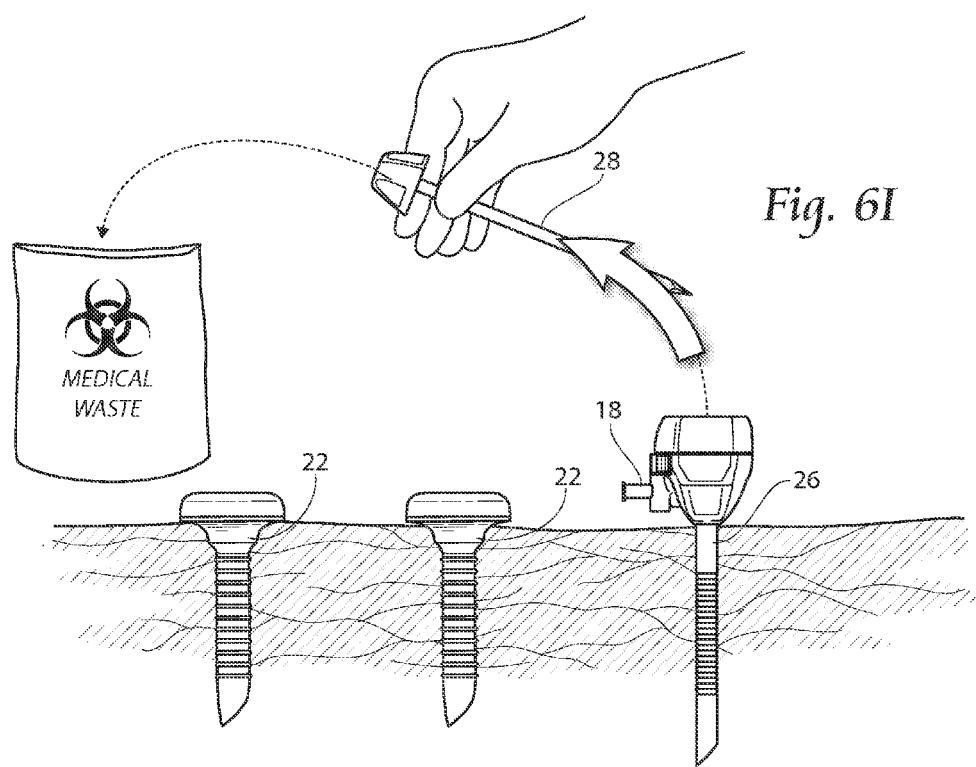

Following (viii) (as FIG. 6I shows), the dedicated functional obturator 28 of the trocar assembly 24 can be discarded as medical waste. A comparison of FIG. 1E (prior art) to FIG. 6I graphically demonstrates the significant reduction in environmental damage due to medical waste, as well as the contribution to lowered health care costs, that the technical features of the system and method provide.

The system 20 and method make possible the use of a single functional obturator (i.e., the dedicated obturator 28 of the trocar assembly 24) for multiple endoscopic entries. The presence of the cannula unit 22 does not disturb either visualization during entry or significant enlarge the penetration site.

To the extent that several cannula units 22 are installed during a given procedure, only one trocar assembly 24 (comprising only one dedicated functional obturator 28) need be used for the multiple entries. Thus (as FIG. 6I demonstrates), at the end of the procedure, there remains, as medical waste, only a single functional obturator (i.e., the dedicated obturator 28 of the trocar assembly 24), which is significantly less than the number of cannulas and abdominal penetrations deployed during the procedure. Cost savings and less environmental damage result.

B. Second Representative Embodiment (An Overview)

Figure 7:
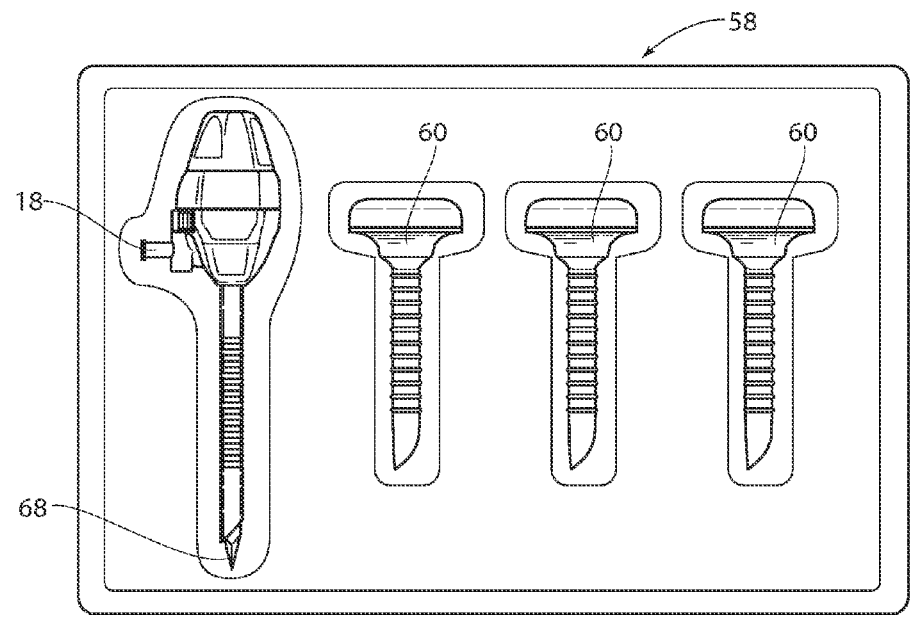
FIG. 7 is a view of another simplified system for performing an endoscopic surgical procedure that makes possible the installation of multiple non-conventional cannula units using a single conventional functional obturator.

FIG. 7 shows another representative embodiment of simplified system 58 for performing an endoscopic surgical procedure. The system 58 solves the problem of excess medical waste and unnecessary medical equipment costs associated with conventional endoscopic procedures. The system 58 solves this problem by providing single use cannula units 60 sized and configured to accommodate a conventional endoscopic instrument (e.g., 5 mm, or 10 mm, or 12 mm), which can be installed in arrays of multiple cannula units 60 using but a single conventional functional obturator 62 that is supplied in a preassembled conventional LT 64 (as a kit with the cannula units 22, or acquired separately and later used in association with the cannula units 22) having a endoscopic cannula 66 with the same interior diameter as the cannula unit 60.

1. The Cannula Units

The system 58 (see FIG. 7) includes a plurality of individual endoscopic cannula units 60 like that previously described, but possessing a diameter suited for passing a conventional endoscopic instrument (e.g., 5 mm, or 10 mm, or 12 mm). The cannula units 60 provide an array of access sites for minimally invasive endoscopic access to and/or visualization of a targeted internal operating field. As shown in FIG. 7, there is no functional obturator preassembled to any cannula unit 60 to aid insertion of the cannula unit 60 into tissue. Each cannula unit 60 is supplied obturator-free.

Except for its interior diameter, the cannula units 60 shown in FIG. 7 desirably possess the same technical features described for the of the cannula units 22 shown in FIG. 2 (and as further shown in FIGS. 4A/B/C and 5A/B/C/D).

2. The Trocar Assembly

The system 58 may include a single trocar assembly 64 (see FIG. 7). Alternatively, as above described, the cannula units 60 may be provided separately (either alone or as a plurality), and the obturator 62 used for their passage obtained from a conventional LT obtained from another source. Like the cannula unit 60, the trocar assembly 64 possesses a diameter accommodating a conventional endoscopic instrument (e.g., 5 mm, or 10 mm, or 12 mm), and can itself comprise a convention LT. As earlier described (and as shown in FIG. 3A), the trocar assembly 64 includes a single endoscopic cannula 66, which provides one additional site for endoscopic access to the operating field. The trocar assembly 64 also includes, for the cannula, a single dedicated functional obturator 62 to aid insertion of the trocar assembly 64 as a unit into tissue. The single dedicated functional obturator 62 of the trocar assembly 64 is the only functional obturator the system 58 provides.

3. Representative Method of Use

The unique functional features of each cannula unit as described make possible a unique method of establishing an array of multiple endoscopic access sites using only a single functional obturator. FIGS. 8A to 8I show a representative method that makes use of these features.

The method includes (see FIG. 8A) (i) providing a single endoscopic trocar assembly 64 comprising a single endoscopic cannula 66 and a single, dedicated functional obturator 62, as described above.

The method further includes (see FIG. 8B) (ii) providing one or more endoscopic cannula units 60, as described above, free of (i.e., without) its own dedicated functional obturator. Each cannula unit 60 has an interior diameter sized and configured to smoothly and tightly accommodate passage of the obturator 62 when removed from the trocar assembly 64 (which can comprise a conventional LT), after that trocar assembly 64 (or conventional LT) has been passed through the abdominal wall and the obturator 62 removed so it can be reused. The cannula unit 60 has a maximum axial length that is equal to or less than the maximum axial length of the endoscopic cannula 66 of the trocar assembly 64 (or conventional LT).

Figure 8A:
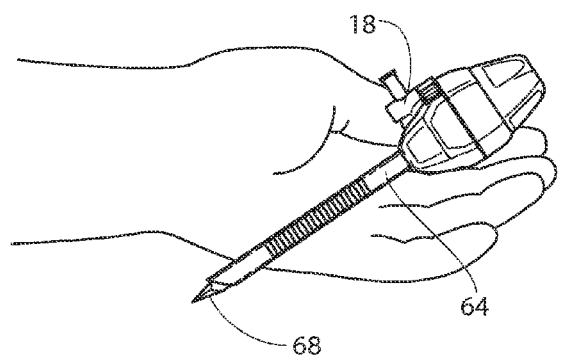
FIGS. 8A to 8H are a sequence of views showing a representative method of using the simplified system shown in FIG. 7.
Figure 8B:
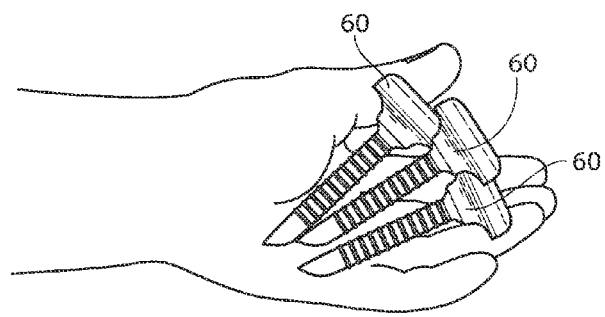
Figure 8C:
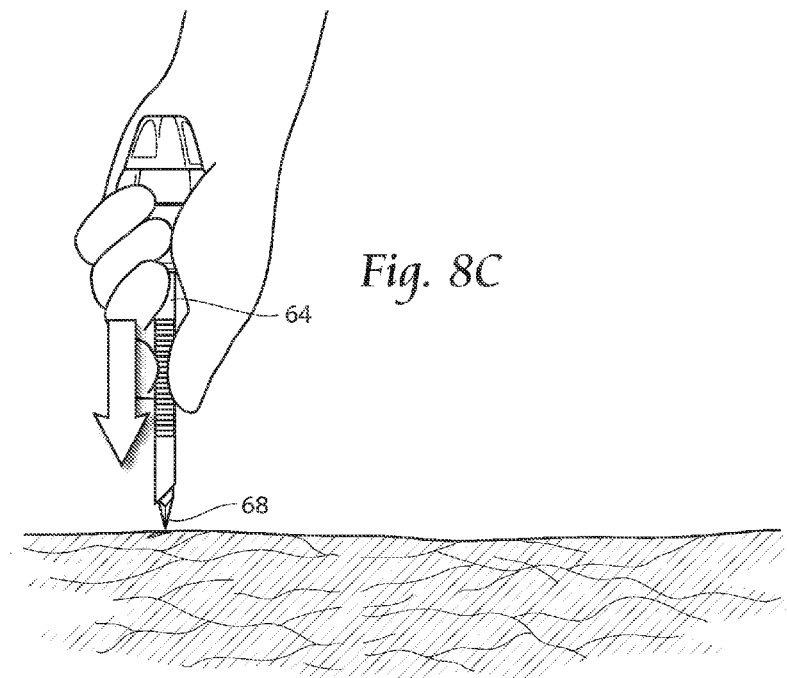
Figure 8D:
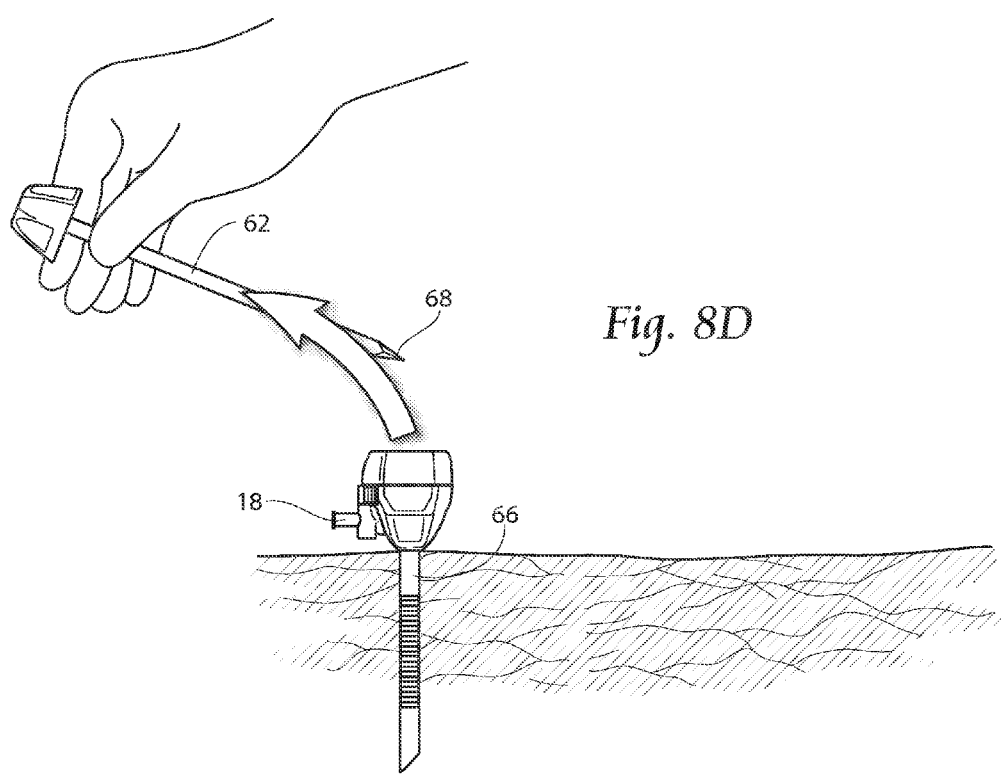

The method further includes, prior to insertion of any of the cannula units 60 (see FIG. 8C), (iii) the use of the trocar assembly 64 (or conventional LT) by itself in a traditional manner for form an access site. As shown in FIG. 8C, the method includes manipulating the trocar assembly 64 (or conventional LT) as an integrated unit into tissue, allowing the protruding, penetrating tip 68 of the functional dedicated obturator 62 to incise or separate tissue to achieve body penetration for the cannula 66. The method further includes, after body penetration has been made (see FIG. 8D), (iv) withdrawing the dedicated functional obturator 62 of the trocar assembly 64 (or conventional LT) from the endoscopic cannula 66 of the trocar assembly 64 (or conventional LT), leaving the endoscopic cannula 66 of the trocar assembly 64 (or conventional LT) in place providing access to the operating cavity. At this stage in the procedure, an insufflation line can be connected to a stopcock 18 conventionally provided on the trocar assembly 64, to pressurize the operating cavity.

The method further includes, after insertion of the cannula 66 of the trocar assembly 64 (or conventional LT) (see FIG. 8E), selecting a single one of the cannula units 60 for inserting into tissue to provide a site of minimally invasive, endoscopic access to a targeted internal operating field, and fitting the selected cannula unit 66 over the functional obturator 62 withdrawn from the trocar assembly 64 (or conventional LT).

Figure 8E:
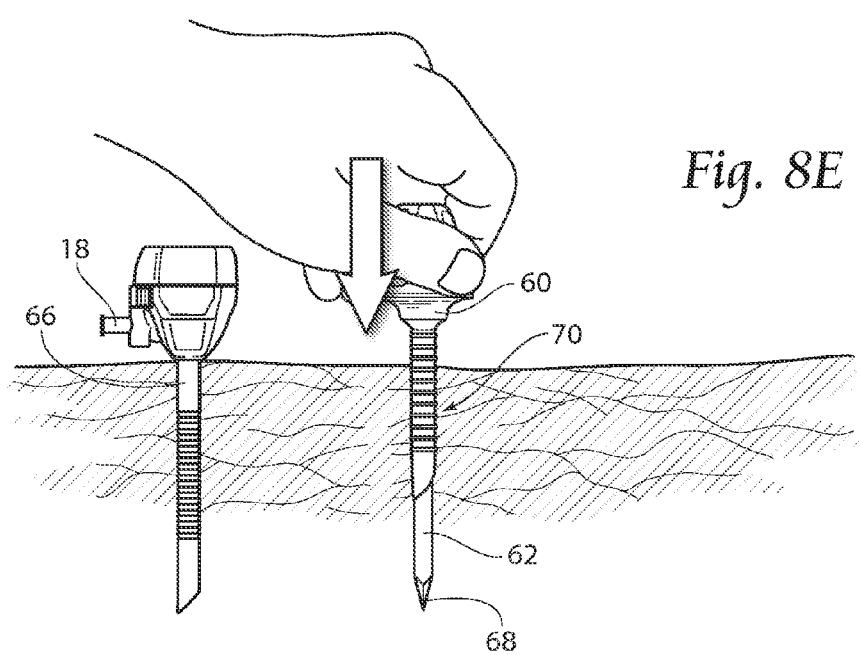
Figure 8F:
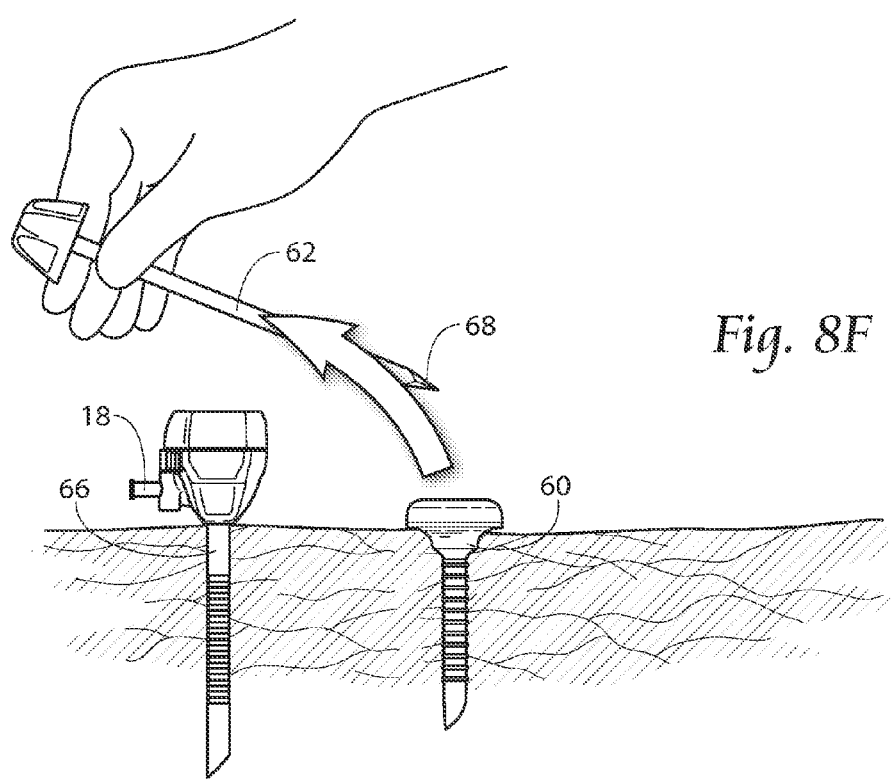
Figure 8G:
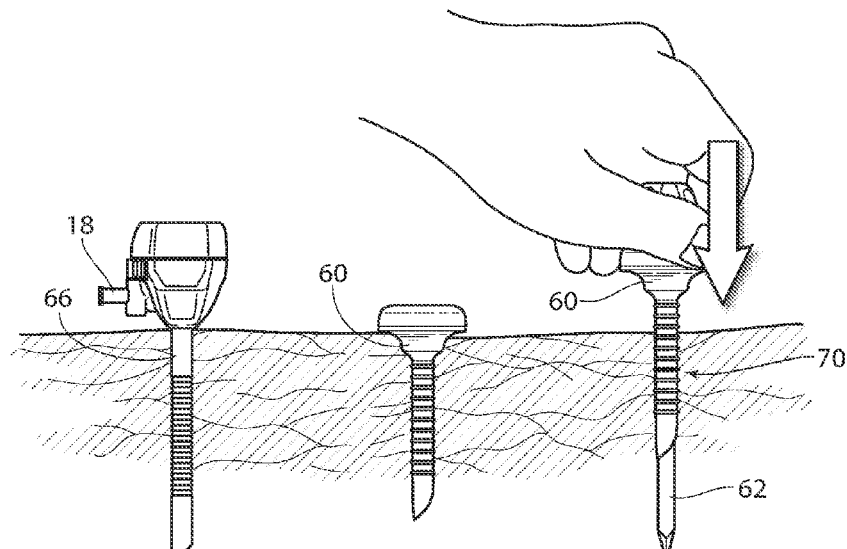
Figure 8H:
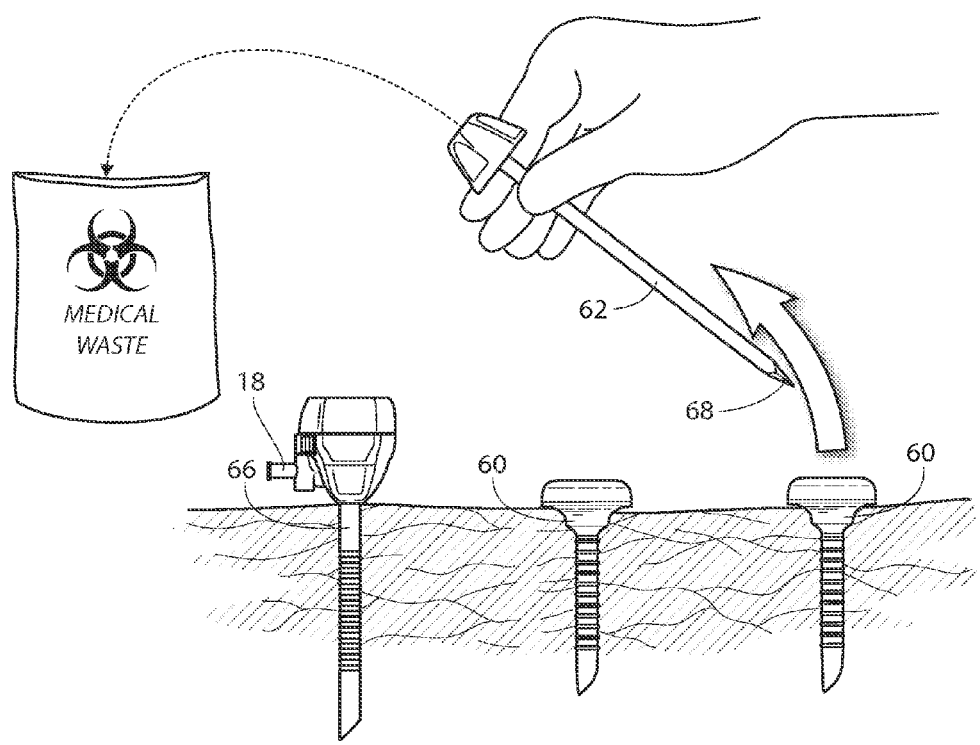

As FIG. 8E shows, by fitting the cannula unit 60 over the functional obturator 62 withdrawn from the trocar assembly 64 (or conventional LT), a concentric access assembly 70 for the cannula unit 60 is created. The concentric access assembly 70 comprises, from interior to exterior, the functional obturator 62 withdrawn from the trocar assembly 64 (or conventional LT) and the selected cannula unit 60. The concentric access assembly 70 includes, protruding beyond the distal end of the cannula unit 60, the penetrating tip 68 of the functional obturator 62.

As FIG. 8E shows, the method further includes (v) manipulating the concentric access assembly 70 as an integrated unit into tissue, allowing the protruding, penetrating tip 68 of the functional obturator 62 to incise or separate tissue to achieve body penetration.

The method further includes, after body penetration of the cannula unit 60 has been made (see FIG. 8F), (vi) withdrawing the functional obturator 62 from the cannula unit 60, leaving the cannula unit 60 in place providing access to the operating cavity. A gas seal assembly 36 in the cannula unit 60, as above described, prevents loss of insufflation pressure as the method progresses.

The method optionally includes, after (vi) (see FIGS. 8H and 8I) the repeated reuse of the functional obturator 62 withdrawn from the trocar assembly 64 (or conventional LT) to install any desired number of selected cannula units 60 to provide any desired number of abdominal penetrations. For each abdominal penetration, a given cannula unit 60 is fitted concentrically over the functional obturator 62 withdrawn from the trocar assembly 64 (or conventional LT), to form a concentric access assembly 70 that includes the additionally selected cannula unit 60. The concentric access assembly 70 is again manipulated as a single unit, allowing the protruding, penetrating tip 68 of the functional obturator 62 to again incise or separate tissue and again achieve body penetration. Once penetration has been made (see FIG. 8I), the functional obturator 62 is withdrawn from the cannula unit 60. Another selected cannula unit 60 remains to provide additional access to the operating cavity.

Following (vi) (as FIG. 8I shows), the dedicated functional obturator 62 of the trocar assembly 64 (or conventional LT) can be discarded as medical waste. A comparison of FIG. 1E (prior art) to FIG. 8I graphically demonstrates the significant reduction in environmental damage due to medical waste, as well as the contribution to lowered health care costs, that the technical features of the system and method provide.

The system 58 and method make possible the use of a single functional obturator (i.e., the dedicated obturator 62 of the trocar assembly 64 or conventional LT) for multiple endoscopic entries. The presence of the cannula unit 60 does not disturb either visualization during entry or significant enlarge the penetration site.

To the extent that several cannula units 60 are installed during a given procedure, only one trocar assembly 64 or conventional LT (comprising only one dedicated functional obturator 62) need be used for the multiple entries. Thus (as FIG. 81 demonstrates), at the end of the procedure, there remains, as medical waste, only a single functional obturator 62 (i.e., the obturator of the trocar assembly 64 or conventional LT), which is significantly less than the number of cannulas and abdominal penetrations deployed during the procedure. Cost savings and less environmental damage result.

II. Creating Endoscopic Access for a Specialized View Optimizing Assembly

A. Overview

Figure 9:
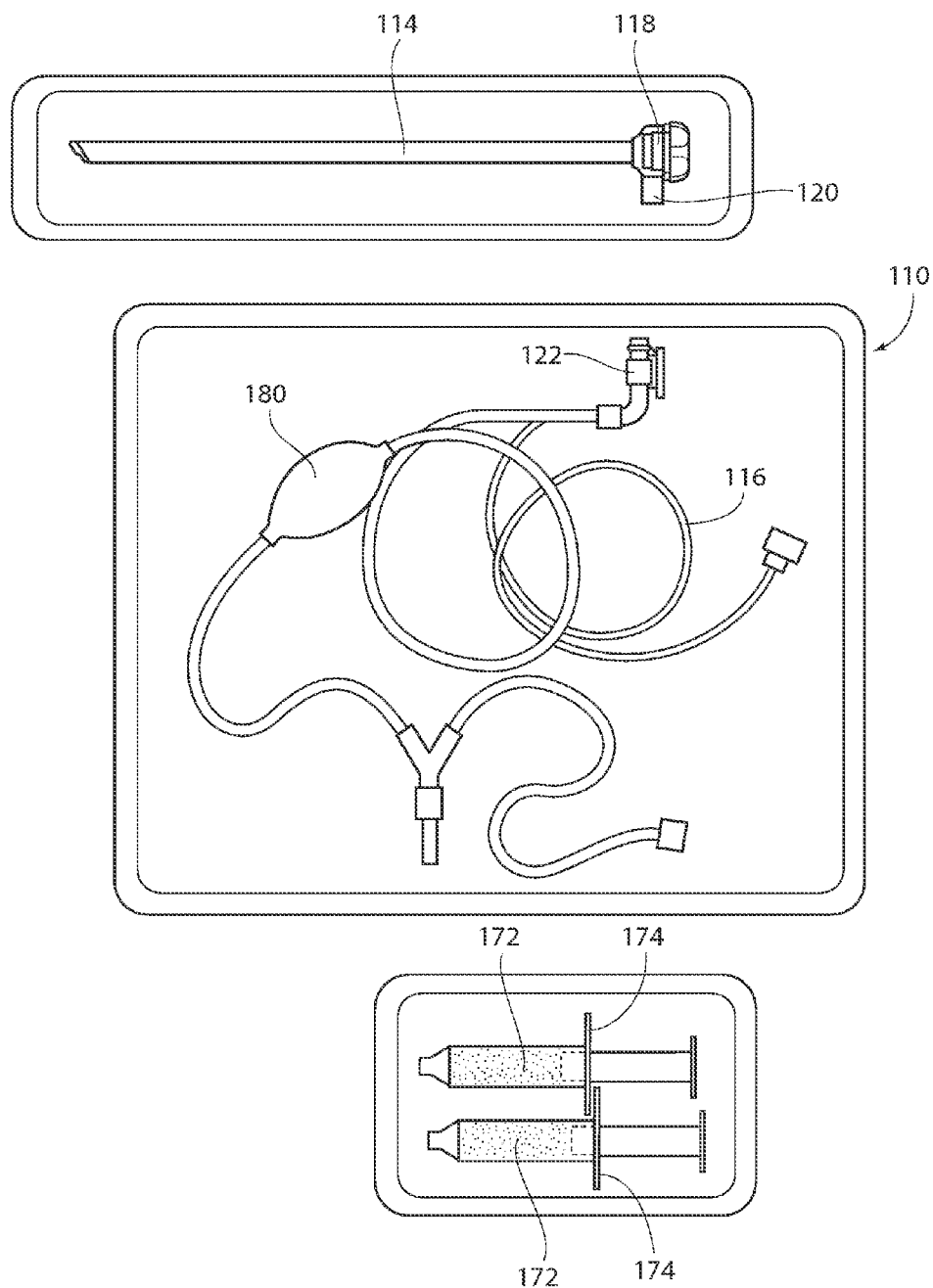
FIG. 9 is a view of a view optimizing assembly for use with a state of the art laparoscope.
Figure 10A:
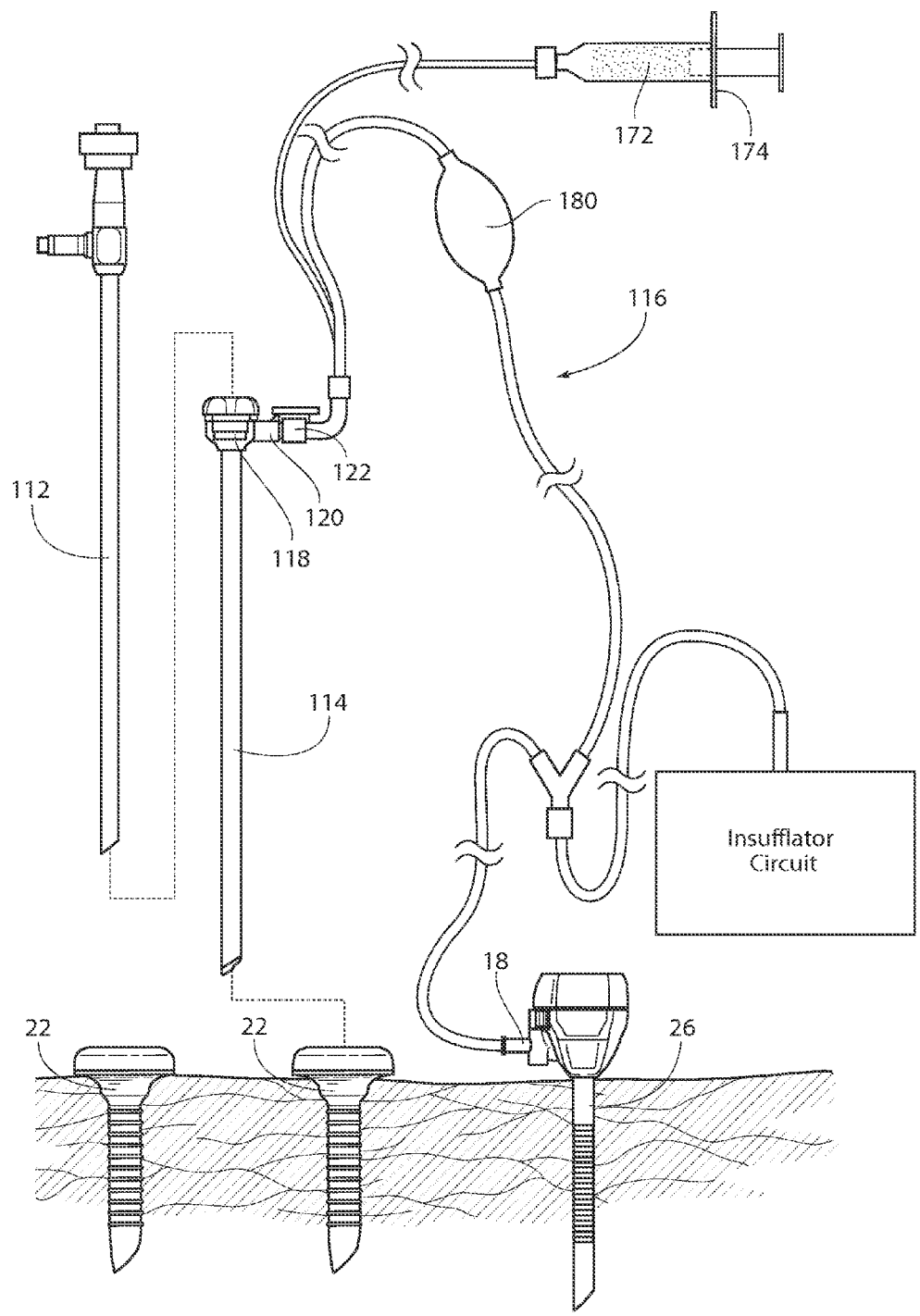
FIGS. 10A to 10C are a sequence of views showing a representative method of using the view optimizing assembly shown in FIG. 9 is association with the system shown in FIG. 2.
Figure 10B:
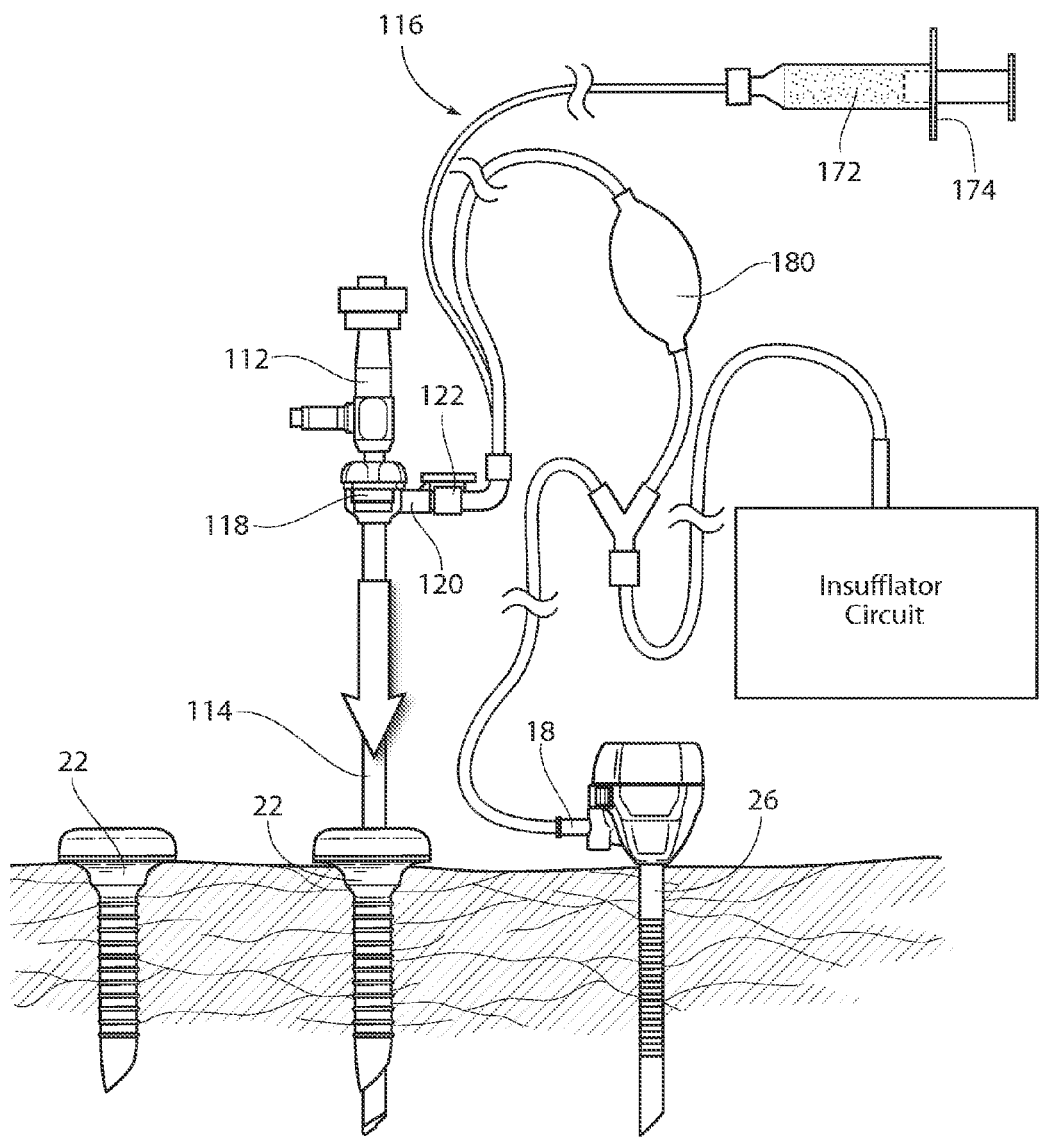
Figure 10C:
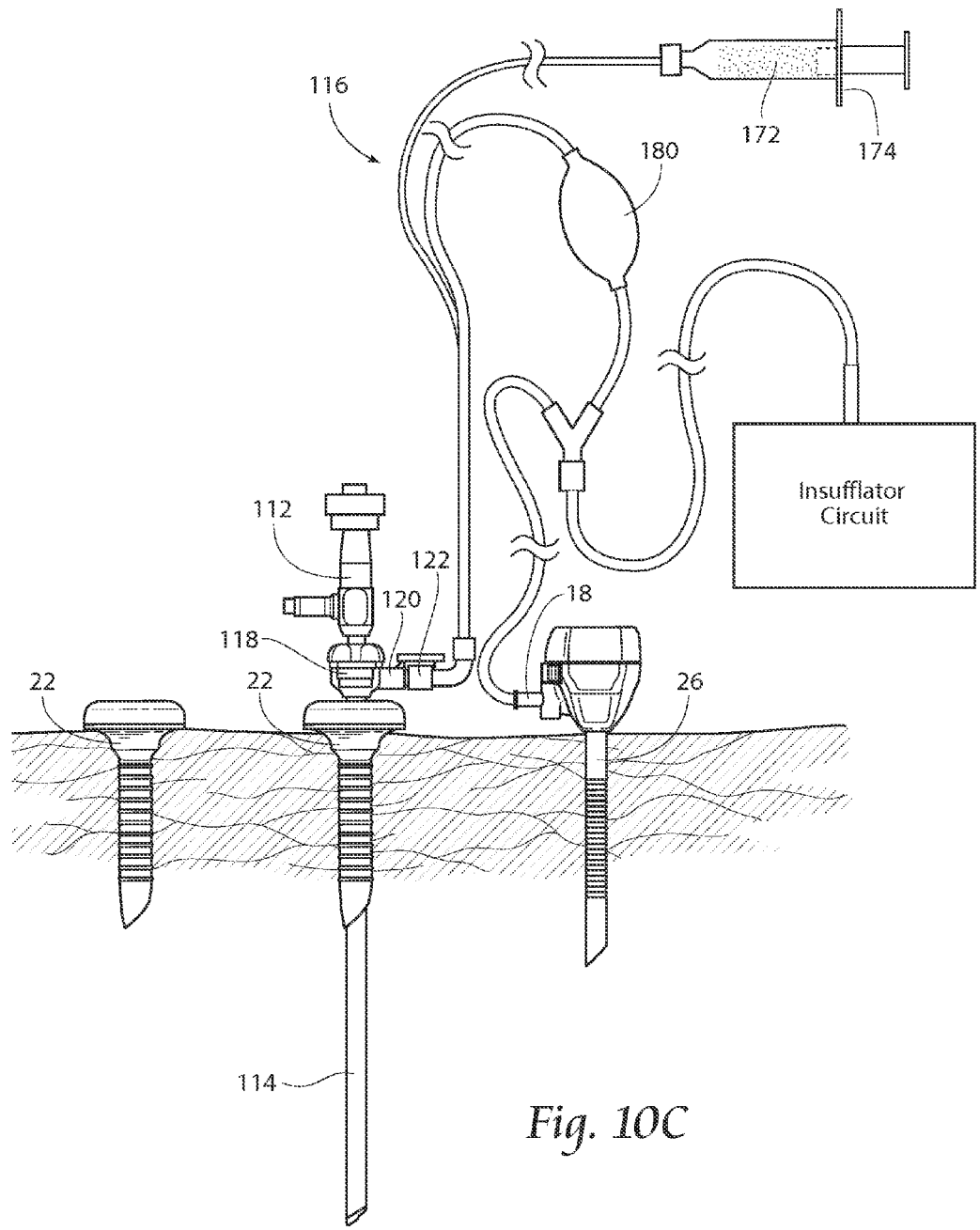

FIG. 9 shows an embodiment of a view optimizing assembly 110 for use in association with a state of the art laparoscope 112 (as shown in FIGS. 10A to 10C). The components of the view optimizing assembly 110 may be made from plastic materials (extruded and/or molded), but other suitable materials, such as metal or a composite material, or combinations thereof could be used.

As shown in FIG. 9, the view optimizing assembly 110 comprises a multi-lumen sheath assembly 114. The sheath assembly 114 is sized and configured to mount over the shaft of a conventional laparoscope 112, as FIGS. 10A and 10B show. The end of the sheath 114 is sized and configured to match the size and configuration of the end of the corresponding laparoscope 112, which in FIG. 10A is shown to be angled.

As FIG. 9 shows, the assembly 110 includes a tubing set 116 and a source of flushing liquid 172. In the illustrated embodiment, the source of flushing liquid 172 comprises a syringe 174, which contains the flushing liquid 172. The flushing liquid 172 can include a surface-active agent (surfactant) to aid removal of fatty debris. For example, the flushing liquid 172 can be a solution comprising (i) Docusate Sodium: 0.050-0.20% v/v; (ii) Phosphate Buffer: 0.2% v/v; and (iii) Water for Injection H2O: 99.600-99.75%. The flushing liquid 172 is packaged in a 10 ml or 20 ml syringe 174, sterilized, and delivered to the surgical suite in a double poly pouch, as FIG. 9 shows.

As FIG. 10A shows, in use, the tubing set 116 connects the sheath 114 to a carbon dioxide (CO2) insufflation circuit, as well as to the syringe 174 containing the flushing liquid 172. As FIG. 10A also shows, a manifold 118 on the proximal end of the sheath 114 includes a quick exchange coupling 120 that mates with a quick exchange coupler 122 on the tubing set 116, to quickly couple the tubing set 116 in fluid communication with the interior lumens of the sheath 114.

Figure 11A:
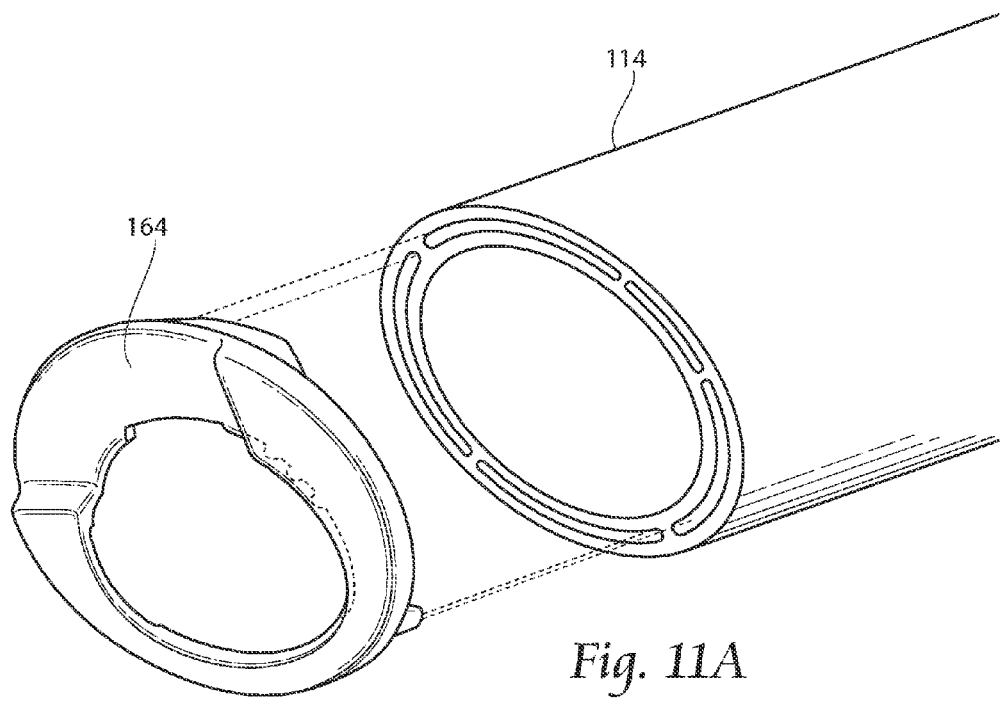
FIGS. 11A to 11C are enlarged views showing the details of the deflector assembly that forms a part of the view optimizing assembly shown in FIG. 9 that prevents fogging of the laparoscopic lens and deflects smoke and debris away from the lens during surgery.
Figure 11B:
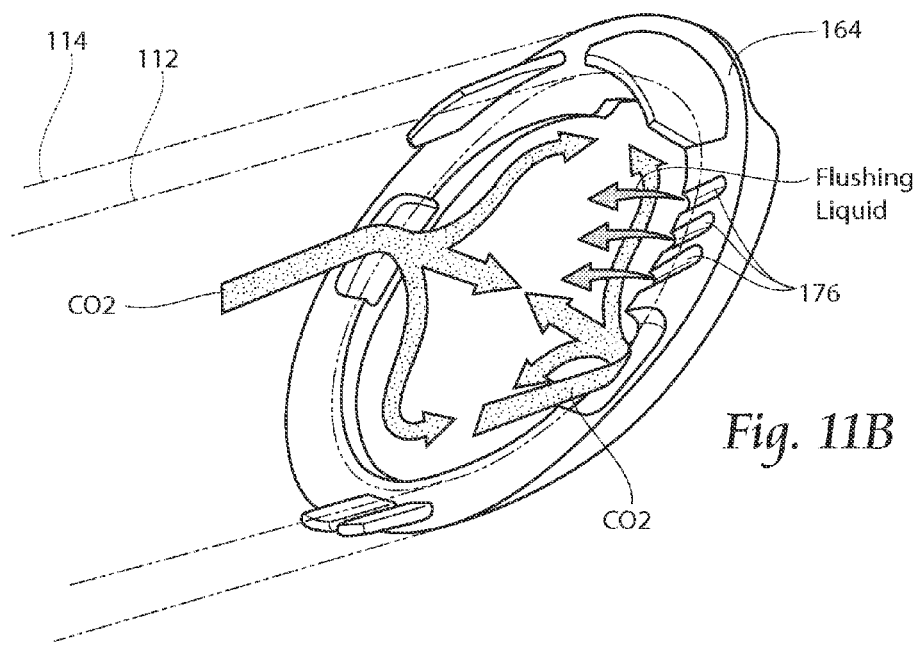

The sheath 114 includes at its distal end a deflector assembly 164 (see FIGS. 11A and 11B). The deflector assembly 164 projects a predetermined distance beyond the distal end of the sheath 114, and thus also a predetermined distance beyond the lens at the distal end of the laparoscope 112.

Figure 11C:
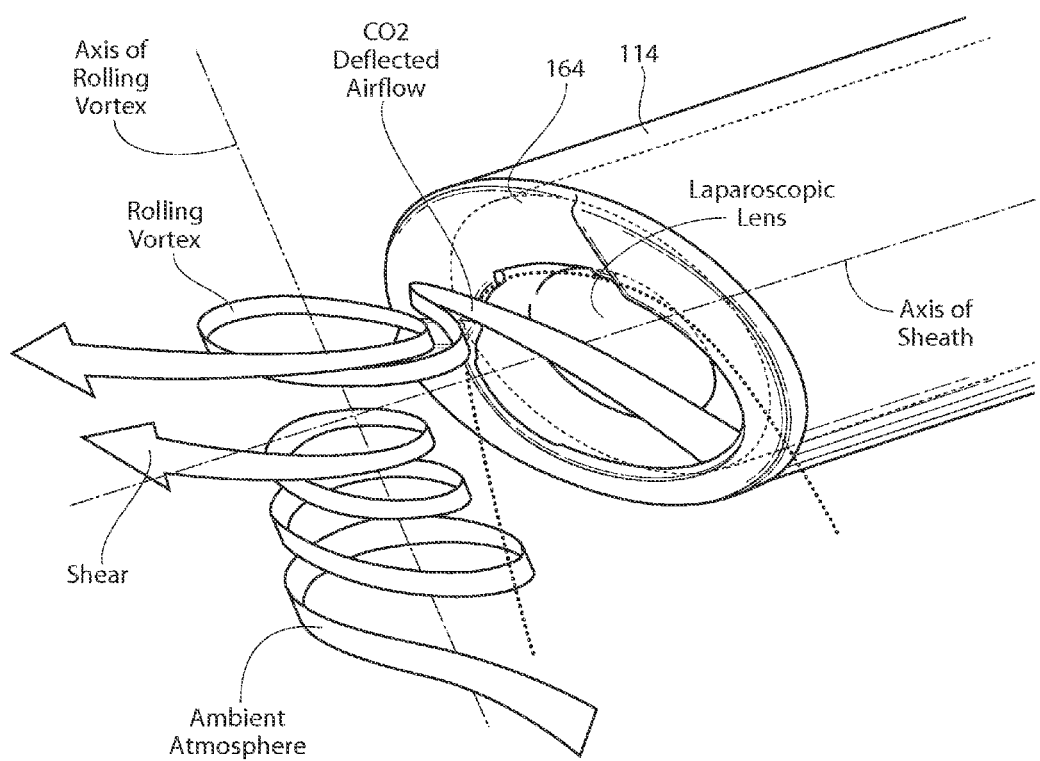

As FIG. 11B shows, the deflector assembly 164 is sized and configured to direct the CO2 gas that is conveyed along the sheath 114 through lumens in a prescribed flow path and flow velocity across the laparoscopic lens. As FIG. 11C shows, a rolling vortex can be created that extends across and beyond the laparoscopic lens. The flow path and flow velocity of the CO2 across the laparoscopic lens prevents fogging and also desirably serves to deflect smoke and surgical debris away from the laparoscopic lens during surgery, thereby maintaining clear visualization of the surgical site without removing the laparoscope from the abdominal cavity for the purpose of cleaning or de-fogging its lens.

The surgical team may also depress the plunger of the syringe plunger 174 to dispense aliquots of 1 ml-5 ml of the flushing liquid 172 through the deflector assembly 164 (which conveyed through other lumens in the sheath) to flush debris off the end of the lens that may eventually accumulate.

The operator can, if desired, prompt a burst of CO2 gas from the insufflation circuit over the lens (by squeezing the pneumatic flush bulb 180 in the tubing set 116), to further remove debris and/or residual droplets of the flushing liquid from the lens. Visualization is restored rapidly and without removal of the laparoscope from the abdomen.

It is desirable to integrate the assembly 110 as much as possible with the existing suite of minimally invasive instrumentation, to not interfere with the surgical set-up, and to require minimal change in the process or practice of the surgical team.

As above explained, conventional laparoscopes, like other laparoscopic tools, typically come in three standard diameter sizes: 5 mm, 10 mm, and 12 mm. To meet the above-stated desirable objective, the sheath assembly 114 is desirably sized with an interior diameter to accommodate a selected one of these laparoscope diameters, as well as with an exterior diameter to accommodate passage through a conventional LT.

The sheath 114, when sized and configured to provide its desirable functional benefit for the smallest diameter conventional laparoscope (5 mm), possesses a marginally increased exterior diameter that falls between the cannula sizes used by conventional LT's. For example, the sheath 114 with an interior diameter sized for a 5 mm laparoscope has an exterior diameter which is larger than 5 mm, e.g., 7.5 to 8 mm. Although having an interior lumen sized for a conventional 5 mm instrument, the resulting 7-8 mm outer diameter of the sheath 14 is too large to fit a conventional 5 mm LT, and small enough to not require a conventional 10 mm LT.

This problem is effectively overcome by use of the system 20 shown in FIG. 2. The system 20, as previously described, provides a non-conventional cannula unit 22 to accommodate the marginally larger endoscopic dimensions of the sheath 14 (e.g., 7 to 8 mm), but nevertheless accommodating installation using a single smallest conventional 5 mm LT (e.g., 5 mm) (as shown in FIGS. 6A to 6I). Concurrently, use of the system 20 shown in FIG. 2 leads to additional benefits, including significantly less medical waste, as well as lowered health care equipment costs.

FIG. 10A shows the set up of the view optimizing assembly 110 with the system 20 comprising multiple access sites established by practicing the method shown in FIGS. 6A to 6I.

The method makes use of a single 5 mm endoscopic trocar assembly 24 (see FIG. 6A) and one or more marginally enlarged endoscopic cannula units 22 (see FIG. 6B). Each cannula unit 22 has an interior diameter sized and configured to smoothly and tightly accommodate passage of the 5 mm endoscopic cannula 26, which forms the exterior of the single trocar assembly 24. As a consequence, the exterior diameter of each cannula unit 22 is marginally increased.

The method selects a single one of the cannula units for inserting into tissue. The method fits the selected cannula unit 22 over the entire single trocar assembly 24 (FIG. 6C) to form a concentric access assembly 56, and manipulates the concentric access assembly 56 as an integrated unit into tissue (FIG. 6D). At this stage in the procedure, an insufflation line can be connected to the stopcock 18 provided on the trocar assembly 24, to pressurize the operating cavity.

After body penetration and insufflation have been accomplished (see FIG. 6E), the trocar assembly 24 is withdrawn from the cannula unit 22, leaving the cannula unit 22 in place, providing access to the operating cavity. The gas seal assembly 36 in the cannula unit 22, as above described, prevents loss of insufflation pressure as the method progresses.

The method optionally includes (see FIGS. 6F and 6G) the repeated reuse of the single trocar assembly 24 to install any desired number of selected cannula units 22, thereby providing any desired number of abdominal penetrations. In the illustrated embodiment (shown in FIG. 10A), two cannula units 22 are installed. One of these cannula units 22 will ultimately accommodate passage of the sheath 114 (as shown in FIGS. 10B and 10C).

After insertion of all desired cannula units 22, the trocar assembly 24 is itself inserted in a traditional manner, to form yet another access site (FIGS. 6H and 6I). As shown in FIG. 10A, the dedicated functional obturator 28 of the trocar assembly 24 is withdrawn from the endoscopic cannula 26 of the trocar assembly 24, leaving the endoscopic cannula 26 of the trocar assembly 24 in place providing additional access to the operating cavity as well as a site to couple an insufflation pressure line (i.e., to stopcock 18). The entire system 20 shown in FIG. 10A has been installed using but one functional obturator, which can later be discarded as medical waste, or reprocessed (see FIG. 6I).

As FIG. 10A shows, the tubing set 116 of the assembly 10 couples the insufflation circuit to the stopcock 18 of the cannula 26. As FIGS. 10B and 10C show, the laparoscope 112 is inserted into the sheath 114, and the sheath 114 and laparoscope 112 are inserted as a unit through one of the installed cannula units 22.

The system 20 and method therefore make possible the use of a single functional obturator (i.e., the dedicated obturator 28 of the trocar assembly 24) for multiple endoscopic entries. The presence of the cannula unit 22 does not disturb either visualization during entry or significant enlarge the penetration site. Only one trocar assembly 24 (comprising only one dedicated functional obturator 28) need be used for the multiple entries. Thus (as FIG. 6I demonstrates), at the end of the procedure, there remains, as medical waste, only a single functional obturator (i.e., the dedicated obturator 28 of the trocar assembly 24), which is significantly less than the number of cannulas and abdominal penetrations deployed during the procedure. Cost savings and less environmental damage result.

B. Continuous Flow Tubing (CFT)

Figure 12A:
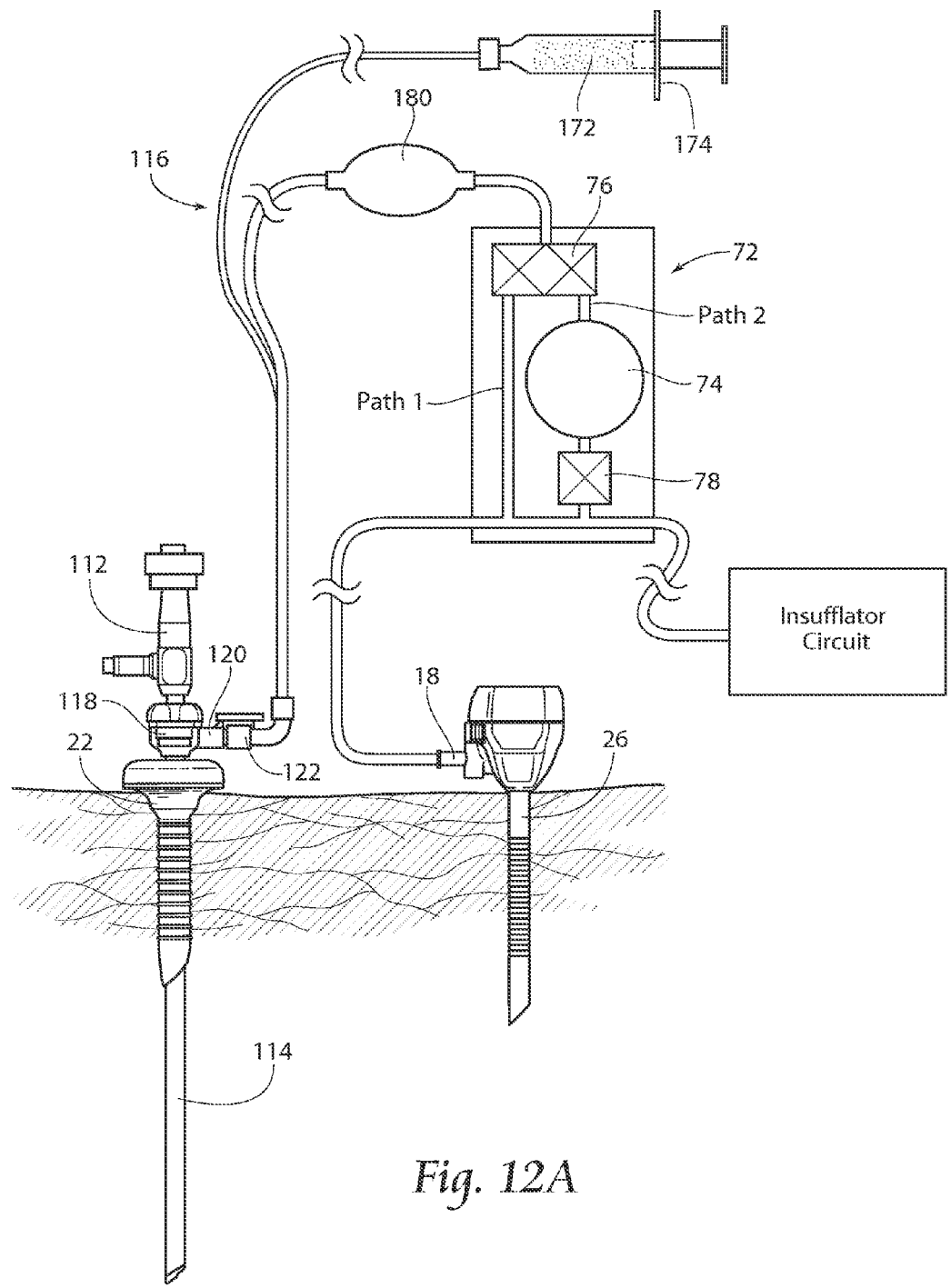
FIGS. 12A and 12B are alternative views of a continuous flow tubing assembly that can be used in conjunction with the view optimizing assembly shown in FIG. 9.
Figure 12B:
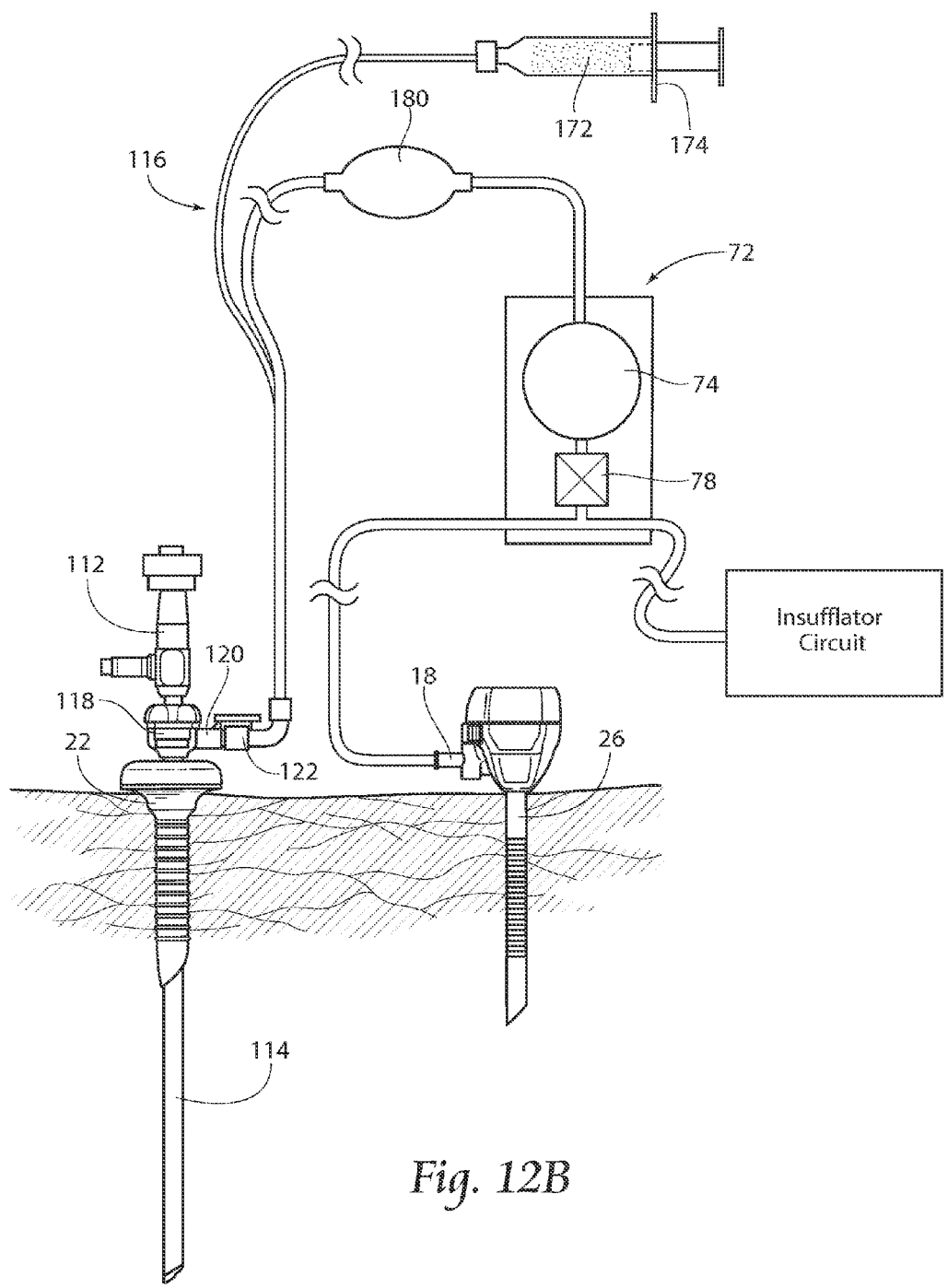

A conventional insufflation circuit periodically cycles off, to stop the flow of $CO_2$ gas to measure the pressure in the peritoneum. As shown in FIGS. 12A and 12B, the tubing set 116 can include a continuous flow tubing assembly 72 (called in shorthand, continuous flow tubing, or CFT), to store pressurized $CO_2$ gas in a reservoir 74, so that when the insufflation circuit stops the flow of gas to measure the pressure in the peritoneum, the flow of gas to sheath 114 is not interrupted. The reservoir 74 serves as a gas capacitor to store $CO_2$ gas at a static pressure reached in the tubing set 116. The reservoir 74 (i.e., gas capacitor) discharges the stored $CO_2$ gas at a controlled rate to the sheath 114 when the flow of gas stops.

As shown in FIGS. 12A and 12B, CFT 72 utilizes a gas reservoir 74 with an elastic diaphragm that expands during filling and maintains a static pressure. The illustrative system shown in FIG. 12A comprises a parallel flow circuit with two flow paths. Path 1 allows for minimal flow reduction when the insufflation circuit is supplying gas and charging the capacitor. Path 2 is operative when the gas capacitor is discharging. A directional valve closes 76 off Path 2 when the insufflations circuit is supplying gas which charges the gas capacitor. The directional valve 76 closes off Path 1 when the insufflation circuit stops supplying gas to measure peritoneum pressure. The static pressure residing in the gas capacitor (i.e., reservoir 74) then discharges to the sheath 114, which maintains a supply of gas across the laparoscope lens. A one-way valve 78 before the gas reservoir allows the gas capacitor to fill when the insufflation circuit is supplying gas and it prevents the back flow of gas when the insufflation circuit is measuring pressure inside the peritoneal space.

The directional valve 76 includes an interior ball that shifts side to side to block the flow paths. The ball is shifted by the pressure differential found between Paths 1 and 2.

The gas capacitor comprises an elastomeric reservoir 74 that expands to store approximately 50 cc of gas under pressure. The reservoir stores gas at 22 mmHg-24 mmHg. The diaphragm is made from a biocompatible elastomer like silicone. Durometer is less than 25 shore A.

The one-way valve 78 can comprise a high flow, low cracking pressure, ball check valve.

The connectors to the CFT 72 can comprise standard luer fittings.

The illustrative CFT 72 shown in FIG. 12B comprises a series flow circuit, in which gas flow to the sheath 114 (downstream of the branch leading to the abdominal cavity) passes through a one-way backflow valve 78 and the reservoir 74 on the way to the sheath 14. When the insufflators cycles off, the one-way valve 78 closes, and static pressure in the reservoir 74 continues to be discharged into the sheath 114.

The concept of CFT 72 comprises the placement of an in-line reservoir (or air capacitor) in the circuit that supplies gas to the sheath 14. The reservoir collects gas during operation of the source insufflator and discharges gas for a brief periods while operation of the insufflator is periodically interrupted. There has never been a reason to provide a reservoir in an insufflations line, because no one has provided medical device that uses insufflation gas for anything but inflating the abdominal cavity.

We claim:

1. An assembly for use with a laparoscope, the assembly comprising:
   a multi-lumen sheath sized and configured to mount over the shaft of the laparoscope, the sheath including a deflector assembly configured to extend a predetermined distance beyond a lens of the laparoscope;
   a tubing set attached to the multi-lumen sheath and configured to connect to an external gas insufflation circuit to deliver gas from the insufflation circuit to flow through at least one lumen of the multi-lumen sheath to the deflector assembly and over the lens of the laparoscope to defog the lens;
   a gas reservoir connected to the tubing set, the gas reservoir configured to store gas when gas from the external insufflation circuit flows through the tubing set and to discharge the stored gas into the multi-lumen sheath in a first path when gas from the external insufflation circuit does not flow through the tubing set so as to provide continuous flow of gas at a prescribed velocity through the multi-lumen sheath;

a one-way valve in the tubing set between the external insufflation circuit and the reservoir, the one-way valve configured to allow gas to flow therethrough from the external insufflation circuit to the reservoir in a second path when gas from the external insufflation circuit flows through the tubing set and configured to prevent gas from flowing therethrough when gas from the external insufflation circuit does not flow through the tubing set; and a bulb on the tubing set configured to deliver a burst of gas through at least one lumen of the multi-lumen sheath to the deflector assembly and over the lens at a velocity over the prescribed velocity to remove debris from the lens of the laparoscope, the bulb in-line with the first path and the second path.

2. The assembly according to claim 1 wherein the sheath further comprises a quick exchange coupling that mates with a quick exchange coupler located on the tubing set.

3. The assembly of claim 1, wherein the tubing set is further configured to connect to a source of flushing liquid to deliver flushing fluid from the source to the multi-lumen sheath.

4. The assembly of claim 1, wherein the gas reservoir is configured to store the gas at a static pressure reached in the tubing set.

5. The assembly of claim 1 wherein the gas reservoir comprises a diaphragm configured to expand as gas is supplied to the gas reservoir.

6. The assembly of claim 5, wherein the diaphragm comprises an elastomer.

7. The assembly of claim 1, further comprising a directional valve in the tubing set between the reservoir and the sheath, the directional valve configured to prevent the flow of stored gas out of the reservoir when gas from the external insufflation circuit flows through the tubing set and to allow the flow of stored gas out of the reservoir when gas from the external insufflation circuit does not flow though the tubing set.

8. The assembly of claim 7, wherein the directional valve is configured to be triggered based upon a pressure differential in the tubing set.

9. The assembly of claim 1, wherein the reservoir is configured to store approximately 50 cc of gas under pressure.

10. The assembly of claim 1, wherein the one-way valve is a ball check valve.

* * * * *